United States Patent

Misawa et al.

[11] Patent Number: 5,948,593
[45] Date of Patent: Sep. 7, 1999

[54] OPTICAL RECORDING MEDIUM

[75] Inventors: Tsutami Misawa; Kenichi Sugimoto; Taizo Nishimoto; Hisashi Tsukahara; Takeshi Tsuda; Keisuke Takuma; Hideki Umehara, all of Kanagawa, Japan

[73] Assignees: Mitsui Chemicals, Inc., Tokyo, Japan; Yamamoto Chemicals, Inc., Osaka, Japan

[21] Appl. No.: 08/898,597

[22] Filed: Jul. 22, 1997

[30] Foreign Application Priority Data

| Jul. 29, 1996 | [JP] | Japan | 8-198944 |
| Jul. 29, 1996 | [JP] | Japan | 8-198945 |
| Dec. 13, 1996 | [JP] | Japan | 8-333752 |

[51] Int. Cl.$^6$ .................................................. G11B 7/24
[52] U.S. Cl. .................. 430/270.16; 430/270.15; 430/945; 430/275.1; 369/284; 369/286; 428/64.8; 428/913; 428/914
[58] Field of Search .............................. 430/945, 270.15, 430/275.1, 127.16; 428/64.8, 913, 914; 369/284, 286

[56] References Cited

U.S. PATENT DOCUMENTS

| 4,735,889 | 4/1988 | Namba et al. | 430/270.19 |
| 4,774,339 | 9/1988 | Haugland et al. | 548/405 |
| 4,916,711 | 4/1990 | Boyer et al. | 252/301.17 |
| 4,950,579 | 8/1990 | Debe et al. | 430/270.16 |
| 5,248,782 | 9/1993 | Haugland et al. | 548/110 |
| 5,274,113 | 12/1993 | Kang et al. | 548/405 |
| 5,433,896 | 7/1995 | Kang et al. | 252/700 |
| 5,486,437 | 1/1996 | Iwamura et al. | 430/270.16 |
| 5,498,641 | 3/1996 | Urano et al. | 522/26 |

FOREIGN PATENT DOCUMENTS

| 238759 | 9/1987 | European Pat. Off. . | |
| 361936 | 4/1990 | European Pat. Off. . | |
| 60-249143 | 12/1985 | Japan | 430/945 |
| 4-009054 | 1/1992 | Japan . | |
| 6-199045 | 7/1994 | Japan . | |
| 562755 | 7/1944 | United Kingdom | 548/402 |
| WO93/09185 | 5/1993 | WIPO . | |

OTHER PUBLICATIONS

Nikkei Electronics, "Optical Recordable Memory Discs Satisfied CD Standard—Recording by Heat Transforming a Substrate and Surface of a Dye Layer", Jan. 23, 1989, No. 465, p. 107 (together with abstract).

Optical Data Storage Digest Series, "That's CD–R", vol. 1, p. 45, 1989.

Nikkei Electronics, "Pioneer has Developed Karaoke Machine Using a High Density Disc", Oct. 11, 1993, No. 592, p. 65 (together with abstract).

(List continued on next page.)

*Primary Examiner*—Martin Angebranndt
*Attorney, Agent, or Firm*—Burns, Doane, Swecker & Mathis, L.L.P.

[57] ABSTRACT

An optical recording medium having at least a recording layer and a reflective layer on a substrate. The recording layer contains a dipyrromethene metal chelate compound obtained from a dipyrromethene compound represented by the general formula (1) and a metal ion:

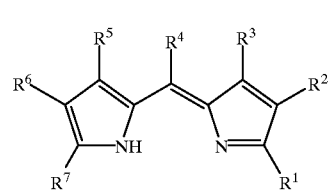

(1)

wherein $R^1$ to $R^7$ are defined in the specification.

8 Claims, 1 Drawing Sheet

OTHER PUBLICATIONS

Nikkei Electronics, "Sanyo Manufactured by Way of Trial Read–Only Optical Disc Having 4 Times Density by CD—Using Red Semiconductor Laser of 635 nm–", Aug. 30, 1993, No. 589, p. 55 (abstract only).

Nikkkei Electronics, "Video CD Standard, Achieving Interactive Software Using Moving Picture or Standstill Picture", Nov. 8, 1993, No. 594, pp. 169–174 (together with abstract).

Applied Phys. Lett., "Blue–Green Laser Diodes", vol. 59, No. 11, Sep. 9, 1991, pp. 1272–1274.

Nikkei Electronics, "Blue–Green Laser Diode, Pulse Oscillation at Room Temperature and Followed Continuous Oscillation at 77K", Apr. 27, 1992, No. 552, pp. 90–91.

Patents Abstracts of Japan, vol. 18, No. 259, (M–1607), May 18, 1994 & JP 06040161A (Nippon Columbia), Feb. 15, 1994 (Abstract Only).

Patent Abstracts of Japan, vol. 10, No. 124 (P–454) "2181!", May 9, 1986 & JP 60249143A (RICOH), Dec. 9, 1985 (Abstract Only).

OPTICAL RECORDING MEDIUM

BACKGROUND OF THE INVENTION (i) Field of the Invention

The present invention relates to a dipyrromethene metal chelate compound, and an optical recording medium in which said compound is used and which is recordable and reproducible at a higher density as compared with a conventional technique.

(ii) Description of the Related Art

As a recordable-type optical recording medium which conforms to compact disc (hereinafter abbreviated to "CD") standards, a CD-R (CD-Recordable) has been suggested and developed {e.g., Nikkei Electronics No. 465, p. 107 (Jan. 23, 1989), and OPTICAL DATA STORAGE DIGEST SERIES, Vol. 1, p. 45 (1989)}. As shown in FIG. 1, this CD-R comprises a transparent resin substrate 1, and a recording layer 2, a reflective layer 3 and a protective layer 4 laminated in this order on the transparent resin substrate 1, and when the recording layer is irradiated with a high power laser light, the recording layer gives rise to a physical or a chemical change to record information in the form of pits. The information in the form of the pits can be reproduced by irradiating a formed pit site with a low power laser light to detect the change of a reflectance. For the record and the reproduction of the optical recording medium, a near infrared semiconductor laser having a wavelength of 770 to 830 nm is usually used, and since the optical recording medium conforms to the standards of CDs such as Red Books and Orange Books, it has a feature that it is compatible with a CD player and a CD-ROM player.

However, a record capacity of the above-mentioned conventional medium is about 650 MB, and when the record of digital movies is taken into consideration, the capacity is insufficient. In recent years, with the remarkable increase of information volume, demands for the enhancement of the density and the capacity of the information recording medium have increased more and more.

Furthermore, the development of short wavelength semiconductor lasers which can be utilized in an optical disc system has advanced, and red semiconductor lasers having wavelengths of 680 nm, 650 nm and 635 nm have been put to practical use {e.g., Nikkei Electronics No. 592, p. 65 (Oct. 11, 1993)}. By shortening the wavelength of the record/reproduction laser and increasing a numerical aperture of an object lens, the size of beam spots can be reduced, which permits the formation of the high-density optical recording medium. In fact, the optical recording medium having the large capacity in which the digital movies can be recorded for a long time has been developed by shortening the wavelength of the semiconductor laser, increasing the numerical aperture of the object lens, or using a data compression technique {e.g., Nikkei Electronics No. 589, p. 55 (Aug. 30, 1993), and No. 594, p. 169 (Nov. 8, 1993)}. Nowadays, there has been developed a digital video disc (DVD) in which the digital movies are recorded for a period of 2 or more hours. The DVD is a read only medium having a record capacity of 4.7 GB, and it has been desired to develop a recordable optical disc suitable for this capacity.

In addition, a laser of 532 nm obtained by high-frequency conversion of a YAG laser has also been put to practical use.

A blue/green semiconductor laser of 490 nm which is far shorter than 532 nm has also be researched, but its practicable level has not been attained {e.g., Applied Physics Letter, p. 1272–1274, Vol. 59 (1991), and Nikkei Electronics No. 552, p. 90 (Apr. 27, 1992)}.

In the case that the short wavelength laser is used, a linear record density and a radial record density of the optical disc can theoretically equally be increased, but under the existing circumstances, it is difficult to increase the radial record density so as to be equal to the linear record density. Since the laser light is diffracted and scattered by grooves or lands, the narrower a track pitch is, the smaller a signal detection light quantity is. It is limited from the viewpoint of a molding technique to narrow the track pitch while maintaining a groove depth sufficient to obtain a tracking signal. Moreover, if the grooves are deep and narrow, it is difficult to form a uniform recording layer. In addition, edges of the grooves and the lands are not smooth but slightly rough, which causes noise. Such a bad influence noticeably occurs at a position where the track pitch is narrow to some extent. Taking these facts into consideration, it can be supposed that when the numerical aperture of the object lens at a wavelength of 520 nm is 0.6, the limit of the groove pitch is about 0.5 $\mu$m.

When a dye layer of the CD-R medium is irradiated with the laser light to bring about a physical change or a chemical change and to thereby form the pits, an optical constant and a decomposition behavior of the dye are important factors for forming the good pits. If the less decomposable dye is used, sensitivity deteriorates, or if the noticeably decomposable or the easily changeable dye is used, the interrelation of the pits and the radial land portions are largely affected, so that the formation of the reliable pits is difficult. In the conventional CD-R medium, a refractive index of the dye layer is low at a laser wavelength which is used at a high record density, and an extinction coefficient is not a suitable value, so that the reflectance is low and a sufficient modulation amplitude cannot be obtained. In addition, the small pits should have been formed by a focused beam, but there are inconveniently formed the pits which are spread so largely as to have a large influence on an environment, and a radial cross talk deteriorates. On the contrary, in some cases, the pits are extremely small, so that the desired modulation amplitude cannot be obtained. Therefore, it is necessary to select the dye for the recording layer having the suitable optical characteristics and decomposition behavior.

For example, Japanese Patent Application Laid-open No. 199045/1994 has suggested an optical recording medium which is recordable and reproducible by a semiconductor laser having a wavelength of 680 nm. In a recording layer of this medium, a cyanine dye is used, and the probability of the high-density record and reproduction is exhibited, but there is not any description that the recording has actually been carried out at the high density.

Furthermore, in U.S. Pat. Nos. 4,774,339, 4,916,711, 5,248,782, 5,274,113 and 5,498,641, there have been disclosed chelate compounds of dipyrromethenes and boron halides, but a description of the optical recording media using these compounds is not present.

SUMMARY OF THE INVENTION

An object of the present invention is to provide a dipyrromethene metal chelate compound, and another object of the present invention is to provide an optical recording medium suitable for a high-density record which contains said compound and which is recordable and reproducible by a short wavelength laser having a wavelength of 520 to 690 nm.

The present inventors have intensively investigated to solve the above-mentioned problems, and as a result, the present invention has now been completed. That is to say, the present invention is as follows:

(1) An optical recording medium having at least a recording layer and a reflective layer on a substrate, said recording layer containing a dipyrromethene metal chelate compound obtained from a dipyrromethene compound represented by the general formula (1) and a metal ion

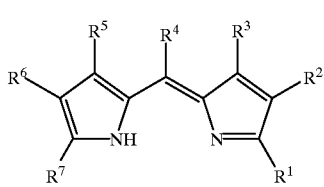

(1)

wherein $R^1$ to $R^7$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkoxy group having 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonyl group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 to 20 carbon atoms, alkylthio group having 1 to 20 carbon atoms, phenylthio group having 6 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(hydroxyalkyl)aminocarbonyl group having 2 to 20 carbon atoms, di(hydroxyalkyl)aminocarbonyl group having 3 to 20 carbon atoms, mono(alkoxyalkyl)aminocarbonyl group having 3 to 20 carbon atoms or di(alkoxyalkyl)aminocarbonyl group having 5 to 20 carbon atoms; $R^2$ and $R^3$ and/or $R^5$ and $R^6$ may bond to each other to form an aromatic ring fused to a pyrrole ring; and the fused aromatic rings formed by these groups may be the same or different and are represented by formula (a):

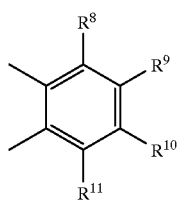

(a)

wherein $R^8$ to $R^{11}$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkoxy group having 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonyl group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 to 20 carbon atoms, alkylthio group having 1 to 20 carbon atoms, phenylthio group having 6 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(hydroxyalkyl)aminocarbonyl group having 2 to 20 carbon atoms, di(hydroxyalkyl)aminocarbonyl group having 3 to 20 carbon atoms, mono(alkoxyalkyl)aminocarbonyl group having 3 to 20 carbon atoms or di(alkoxyalkyl)aminocarbonyl group having 5 to 20 carbon atoms; and $R^{10}$ and $R^{11}$ may bond to each other to form an aromatic ring.

(2) The optical recording medium according to the above-mentioned paragraph (1) wherein the dipyrromethene metal chelate compound is a compound represented by the following general formula (2)

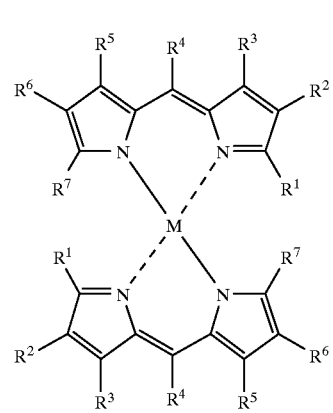

(2)

wherein $R^1$ to $R^7$ are as defined above; and M is a transition element.

(3) The optical recording medium according to the above-mentioned paragraph (1) wherein the dipyrromethene metal chelate compound is a compound represented by the following general formula (3)

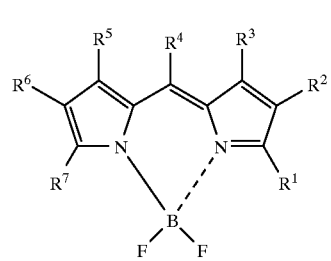

(3)

wherein $R^1$ to $R^7$ are as defined above.

(4) The optical recording medium according to any one of the above-mentioned paragraphs (1) to (3) which is recordable and reproducible by a laser light selected from the wavelength range of 520 to 690 nm.

(5) The optical recording medium according to any one of the above-mentioned paragraphs (1) to (3) wherein, at alaser wavelength, a refractive index of the recording layer is 1.8 or more, and an extinction coefficient of the recording layer is in the range of 0.04 to 0.40.

(6) The optical recording medium according to any one of the above-mentioned paragraphs (1) to (3) wherein a reflectance of a laser light selected from the wavelength range of 520 to 690 nm is 20% or more, as measured from the side of the substrate.

(7) A dipyrromethene metal chelate compound represented by the following general formula (4)

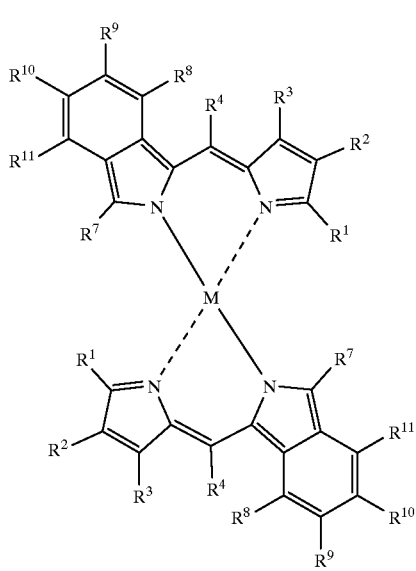

(4)

wherein $R^1$ to $R^4$ and $R^7$ to $R^{11}$ are as defined above; M is a transition element; but $R^2$ and $R^3$ do not form an aromatic ring.

(8) A dipyrromethene metal chelate compound represented by the following general formula (5)

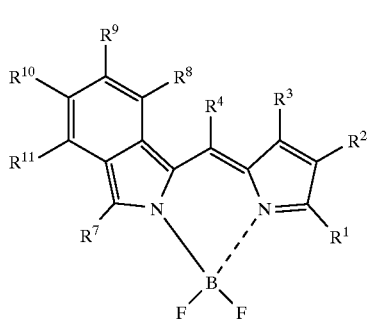

(5)

wherein $R^1$ to $R^4$ and $R^7$ to $R^{11}$ are as defined above; but $R^2$ and $R^3$ do not form an aromatic ring.

According to the present invention, a dipyrromethene metal chelate compound of a dipyrromethene compound and a metal ion is used as a recording layer, whereby a recordable type optical recording medium can be provided which is very noticed as a high-density optical recording medium and which is recordable and reproducible by a laser having a wavelength of 520 to 690 nm.

DETAILED DESCRIPTION OF THE PREFERRED EMBODIMENTS

Figure 1:
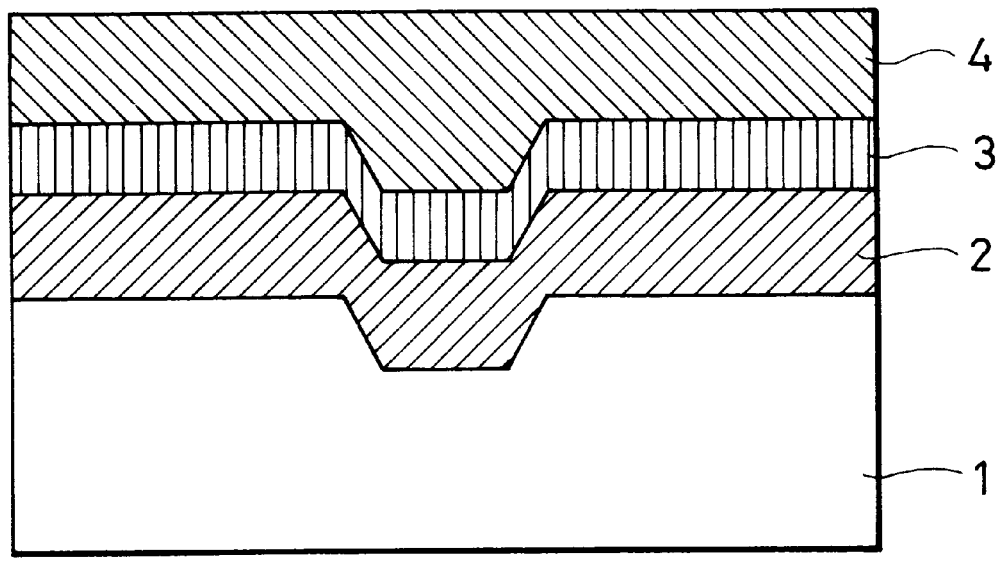
FIG. 1 is a sectional view illustrating a layer constitution of an optical recording medium of a conventional technique and the present invention.

In a dipyrromethene metal chelate compound of a dipyrromethene compound represented by formula (1) and a metal ion according to the present invention, examples of $R^1$ to $R^{11}$ include a hydrogen atom; nitro group; cyano group; hydroxyl group; amino group; carboxyl group; sulfonic acid group; halogen atoms such as fluori ne, chlorine, bromine and iodine;

straight-chain, branched and cyclic alkyl groups having 1 to 20 carbon atoms such as a methyl group, ethyl group, n-propyl group, iso-propyl group, n-butyl group, iso-butyl group, sec-butyl group, t-butyl group, n-pentyl group, iso-pentyl group, 2-methylbutyl group, 1-methylbutyl group, neo-pentyl group, 1,2-dimethylpropyl group, 1,1-dimethylpropyl group, cyclopentyl group, n-hexyl group, 4-methylpentyl group, 3-methylpentyl group, 2-methylpentyl group, 1-methylpentyl group, 3,3-dimethylbutyl group, 2,3-dimethylbutyl group, 1,3-dimethylbutyl group, 2,2-dimethylbutyl group, 1,2-dimethylbutyl group, 1,1-dimethylbutyl group, 3-ethylbutyl group, 2-ethylbutyl group, 1-ethylbutyl group, 1,2,2-trimethylbutyl group, 1,1,2-trimethylbutyl group, 1-ethyl-2-methylpropyl group, cyclohexyl group, n-heptyl group, 2-methylhexyl group, 3-methylhexyl group, 4-methylhexyl group, 5-methylhexyl group, 2,4-dimethylpentyl group, n-octyl group, 2-ethylhexyl group, 2,5-dimethylhexyl group, 2,5,5-trimethylpentyl group, 2,4-dimethylhexyl group, 2,2,4-trimethylpentyl group, n-octyl group, 3,5,5-trimethylhexyl group, n-nonyl group, n-decyl group, 4-ethyloctyl group, 4ethyl-4,5-methylhexyl group, n-undecyl group, n-dodecyl group, 1,3,5,7-tetraethyloctyl group, 4-butyloctyl group, 6,6-diethyloctyl group, n-tridecyl group, 6-methyl-4-butyloctyl group, n-tetradecyl group, n-pentadecyl group, 3,5-dimethylheptyl group, 2,6-dimethylheptyl group, 2,4-dimethylheptyl group, 2,2,5,5-tetramethylhexyl group, 1-cyclopentyl-2,2-dimethylpropyl group and 1-cyclohexyl-2,2-dimethylpropyl group;

halogenoalkyl groups having 1 to 20 carbon atoms such as a chloromethyl group, dichloromethyl group, fluoromethyl group, trifluoromethyl group, pentafluoroethyl group and nonafluorobutyl group;

alkoxyalkyl groups having 2 to 20 carbon atoms such as a methoxyethyl group, ethoxyethyl group, iso-propyloxyethyl group, 3-methoxypropyl group and 2-methoxybutyl group;

alkoxy groups having 1 to 20 carbon atoms such as a methoxy group, ethoxy group, n-propoxy group, iso-propoxy group, n-butoxy group, iso-butoxy group, sec-butoxy group, t-butoxy group, n-pentoxy group, iso-pentoxy group, neo-pentoxy group, n-hexyloxy group and n-dodecyloxy group;

alkenyl groups having 2 to 20 carbon atoms such as a vinyl group, propenyl group, 1-butenyl group, iso-butenyl group, 1-pentenyl group, 2-pentenyl group, 2-methyl-1-butenyl group, 3-methyl-1-butenyl group, 2-methyl-2-butenyl group, 2,2-dicyanovinyl group, 2-cyano-2-methylcarboxyvinyl group and 2-cyano-2-methylsulfonevinyl group;

alkoxyalkoxy groups having 2 to 20 carbon atoms such as a methoxyethoxy group, ethoxyethoxy group, 3-methoxypropyloxy group and 3-(iso-propyloxy)propyloxy group;

aryloxy groups having 6 to 20 carbon atoms such as a phenoxy group, 2-methylphenoxy group, 4-methylphenoxy group, 4-t-butylphenoxy group, 2-methoxyphenoxy group and 4-iso-propylphenoxy group;

acyl groups having 1 to 20 carbon atoms such as a formyl group, acetyl group, ethylcarbonyl group, n-propylcarbonyl group, iso-propylcarbonyl group, n-butylcarbonyl group, iso-butylcarbonyl group, sec-butylcarbonyl group, t-butylcarbonyl group, n-pentylcarbonyl group, iso-pentylcarbonyl group, neo-pentylcarbonyl group, 2-methylbutylcarbonyl group and nitrobenzylcarbonyl group;

alkoxycarbonyl groups having 2 to 20 carbon atoms such as a methoxycarbonyl group, ethoxycarbonyl group, isopropyloxycarbonyl group and 2,4-dimethylbutyloxycarbonyl group;

alkylaminocarbonyl groups having 2 to 20 carbon atoms such as a methylaminocarbonyl group, ethylaminocarbonyl group, n-propylaminocarbonyl group, n-butylaminocarbonyl group and n-hexylaminocarbonyl group;

dialkylaminocarbonyl groups having 2 to 20 carbon atoms such as a dimethylaminocarbonyl group, diethylaminocarbonyl group, di-n-propylaminocarbonyl group, di-n-butylaminocarbonyl group and N-methyl-N-cyclohexylaminocarbonyl group;

alkylcarbonylamino groups having 2 to 20 carbon atoms such as an acetylamino group, ethylcarbonylamino group and butylcarbonylamino group;

phenylaminocarbonyl groups having 7 to 20 carbon atoms such as a phenylaminocarbonyl group, 4-methylphenylaminocarbonyl group, 2-methoxyphenylaminocarbonyl group and 4-n-propylphenylaminocarbonyl group;

phenylcarbonylamino groups having 7 to 20 carbon atoms such as a phenylcarbonylamino group, 4-ethylphenylcarbonylamino group and 3-butylphenylcarbonylamino group;

phenoxycarbonyl groups having 7 to 20 carbon atoms such as a phenoxycarbonyl group, 2-methylphenoxycarbonyl group, 4-methoxyphenoxycarbonyl group and 4-t-butylphenoxycarbonyl group;

aralkyl groups having 7 to 20 carbon atoms such as a benzyl group, nitrobenzyl group, cyanobenzyl group, hydroxybenzyl group, methylbenzyl group, dimethylbenzyl group, trimethylbenzyl group, dichlorobenzyl group, methoxybenzyl group, ethoxybenzyl group, trifluoromethylbenzyl group, naphthylmethyl group, nitronaphthylmethyl group, cyanonaphthylmethyl group, hydroxynaphthylmethyl group, methylnaphthylmethyl group and trifluoromethylnaphthylmethyl group;

aryl groups having 6 to 20 carbon atoms such as a phenyl group, nitrophenyl group, cyanophenyl group, hydroxyphenyl group, methylphenyl group, dimethylphenyl group, trimethylphenyl group, dichlorophenyl group, methoxyphenyl group, ethoxyphenyl group, trifluoromethylphenyl group, N,N-dimethylaminophenyl group, naphthyl group, nitronaphthyl group, cyanonaphthyl group, hydroxynaphthyl group, methylnaphthyl group and trifluoromethylnaphthyl group;

heteroaryl groups having 5 to 20 carbon atoms such as a pyrrolyl group, thienyl group, furanyl group, oxazoyl group, isoxazoyl group, oxadiazoyl group, imidazoyl group, benzoxazoyl group, benzothiazoyl group, benzimidazoyl group, benzofuranyl group and indoyl group;

alkylthio groups having 1 to 20 carbon atoms such as a methylthio group, ethylthio group, n-propylthio group, isopropylthio group, n-butylthio group, iso-butylthio group, sec-butylthio group, t-butylthio group, n-pentylthio group, iso-pentylthio group, 2-methylbutylthio group, 1-methylbutylthio group, neo-pentylthio group, 1,2-dimethylpropylthio group and 1,1-dimethylpropylthio group;

phenylthio groups having 6 to 20 carbon atoms such as a phenylthio group, 4-methylphenylthio group, 2-methoxyphenylthio group and 4-t-butylphenylthio group;

alkenyloxycarbonyl groups having 3 to 20 carbon atoms such as an allyloxycarbonyl group and 2-butenoxycarbonyl group;

aralkyloxycarbonyl groups having 8 to 20 carbon atoms such as a benzyloxycarbonyl group and phenethyloxycarbonyl group;

alkoxycarbonylalkoxycarbonyl groups having 4 to 20 carbon atoms such as a methoxycarbonylmethoxycarbonyl group, ethoxycarbonylmethoxycarbonyl group, n-propoxycarbonylmethoxycarbonyl group and isopropoxycarbonylmethoxycarbonyl group;

alkylcarbonylalkoxycarbonyl groups having 4 to 20 carbon atoms such as a methylcarbonylmethoxycarbonyl group and ethylcarbonylmethoxycarbonyl group;

mono(hydroxyalkyl)aminocarbonyl groups having 2 to 20 carbon atoms such as a hydroxyethylaminocarbonyl group, 2-hydroxypropylaminocarbonyl group and 3-hydroxypropylaminocarbonyl group;

di(hydroxyalkyl)aminocarbonyl groups having 3 to 20 carbon atoms such as a di(hydroxyethyl)aminocarbonyl group, di(2-hydroxypropyl)aminocarbonyl group and di(3-hydroxypropyl)aminocarbonyl group;

mono(alkoxyalkyl)aminocarbonyl groups having 3 to 20 carbon atoms such as a methoxymethylaminocarbonyl group, methoxyethylaminocarbonyl group, ethoxymethylaminocarbonyl group, ethoxyethylaminocarbonyl group and propoxyethylaminocarbonyl group; and di(alkoxyalkyl)aminocarbonyl groups having 5 to 20 carbon atoms such as a di(methoxyethyl)aminocarbonyl group, di(ethoxymethyl)aminocarbonyl group, di(ethoxyethyl)aminocarbonyl group and di(propoxyethyl)aminocarbonyl group.

No particular restriction is put on a metal which can form the chelate compound together with a dipyrromethene compound represented by formula (1), so long as it usually has an ability of forming the chelate compound together with the dipyrromethene compound. Examples of such a metal include metals in the groups 8, 9 and 10 (the group VIII), the group 11 (the group Ib), the group 12 (the group IIb), the group 3 (the group IIIa), the group 4 (the group IVa), the group 5 (the group Va), the group 6 (the group VIa) and the group 7 (the group VIIa), and preferable examples thereof include transition metals such as nickel, cobalt, iron, ruthenium, rhodium, palladium, copper, osmium, iridium, platinum and zinc.

No particular restriction is put on methods for preparing the dipyrromethene compound represented by formula (1) and the dipyrromethene metal chelate compound according to the present invention, but for example, they can be prepared in accordance with methods described in Aust. J. Chem., Vol. 11, p. 1835–1845 (1965); Heteroatom Chemistry, Vol. 1, No. 5, p. 389 (1990); U.S. Pat. No. 4,774,339; U.S. Pat. No. 5,433,896 and the like. Typically, they can be prepared through the following two-step reaction.

In a first step, a compound represented by formula (6) and a compound represented by formula (7), or a compound represented by formula (8) and a compound represented by formula (9) are reacted in a suitable solvent in the presence of an acid catalyst such as hydrobromic acid or hydrogen chloride to obtain a dipyrromethene compound represented by formula (10). Next, in the second step, the dipyrromethene compound represented by formula (10) is reacted with boron trifluoride, or an acetate or a halide of a metal such as nickel, cobalt, iron, ruthenium, rhodium, palladium, copper, osmium, iridium, platinum or zinc to obtain a desired dipyrromethene metal chelate compound.

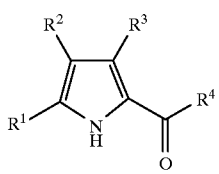
(6)

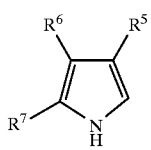
(7)

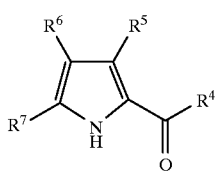
(8)

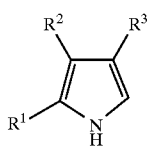
(9)

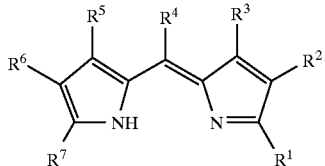
(10)

wherein $R^1$ to $R^7$ are as defined above.

Table 1 shows typical examples of the metal chelate of the dipyrromethene compound represented by formula (1) according to the present invention together with substituents of the above-described formulae (2) to (5) and the following formulae (11) and (12):

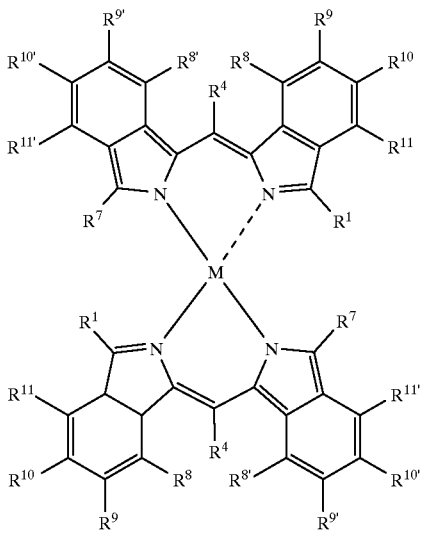
(11)

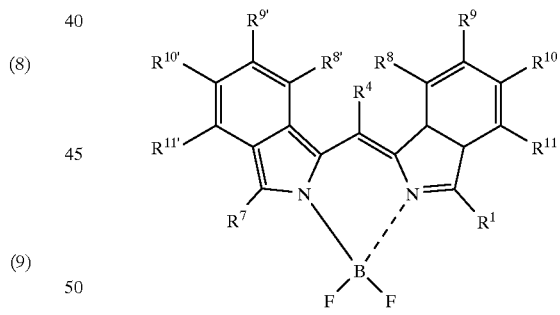
(12)

In Table 1, each compound number shows a corresponding formula number and its serial number, for example, compound number 2-1 means the first example of the compound represented by formula (2).

TABLE 1-1

| Compound | R¹ | R² | R³ | R⁴ | R⁵ | R⁶ | R⁷ | M |
|---|---|---|---|---|---|---|---|---|
| 2-1 | -CH₂-(2,6-dichlorophenyl) | H | H | 2,6-dichlorophenyl | H | H | H | Zn |
| 2-2 | -CH₂-(2,3,5-trimethylphenyl) | H | H | 2,3,5-trimethylphenyl | H | H | H | Zn |
| 2-3 | CH₃ | C₂H₅ | CH₃ | H | CH₃ | C₂H₅ | CH₃ | Zn |
| 2-4 | CH₃ | C₂H₅ | CH₃ | 2,3,5-trimethylphenyl | CH₃ | C₂H₅ | CH₃ | Zn |
| 2-5 | CH₃ | C₂H₅ | CH₃ | H | CH₃ | C₂H₅ | CH₃ | Cu |
| 2-6 | -CH₂-(2-trifluoromethylphenyl) | H | H | 2-trifluoromethylphenyl | H | H | H | Zn |
| 2-7 | COOC₂H₅ | H | H | 4-(dimethylamino)phenyl | H | H | COOC₂H₅ | Cu |
| 2-8 | CH₃ | COOC₂H₅ | CH₃ | H | CH₃ | COOC₂H₅ | CH₃ | Cu |
| 2-9 | COOC₂H₅ | H | H | CN | H | H | H | Cu |
| 2-10 | COOCH₃ | H | H | CN | H | H | COOCH₃ | Fe |

TABLE 1-2

| Compound | R¹ | R² | R³ | R⁴ |
|---|---|---|---|---|
| 2-11 | CH₃ | COOCH₃ | CH₃ | phenyl |

TABLE 1-2-continued

| | | | | |
|---|---|---|---|---|
| 2-12 | CH₃ | CO₂C₂H₅ | CH₃ | 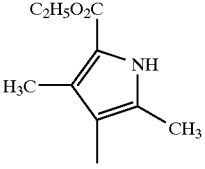 |
| 2-13 | Br | C₂H₅ | CH₃ | H |
| 2-14 | CH₃ | —(CH₂)₂CO₂CH₃ | CH₃ | H |
| 2-15 | —CH₂OCH₃ | C₂H₅ | CH₃ | H |
| 2-16 | 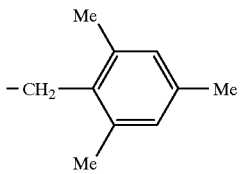 | H | H | 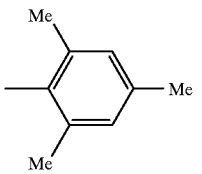 |
| 2-17 | CH₃ | CO₂C₂H₅ | CH₃ | 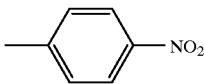 |
| 2-18 | Br | CH₃ | CO₂C₂H₅ | H |
| 2-19 | OCH₃ | CH₃ | C₂H₅ | H |
| 2-20 | 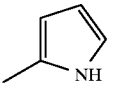 | H | OCH₃ | H |
| 2-21 | CH₃ | H | CH₃ | H |
| 2-22 | CO₂C₂H₅ | Cl | Cl | H |
| 2-23 | CH₃ | —(CH₂)₂CH₃ | H | —(CH₂)₃CH₃ |

| Compound | R⁵ | R⁶ | R⁷ | M |
|---|---|---|---|---|
| 2-11 | CH₃ | COOCH₃ | CH₃ | Ni |
| 2-12 | CH₃ | CO₂C₂H₅ | CH₃ | Ni |
| 2-13 | C₂H₅ | CH₃ | Br | Co |
| 2-14 | —(CH₂)₂CO₂CH₃ | CH₃ | Br | Co |
| 2-15 | CH₃ | C₂H₅ | —CH₂OCH₃ | Ni |
| 2-16 | H | H | 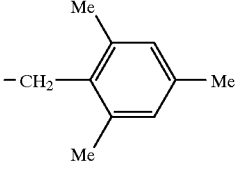 | Zn |
| 2-17 | CH₃ | CO₂C₂H₅ | CH₃ | Cu |
| 2-18 | CO₂C₂H₅ | CH₃ | Br | Pd |
| 2-19 | H | H | H | Zn |
| 2-20 | H | H | —(CH₂)₂CH₃ | Zn |
| 2-21 | CH₃ | H | CH₃ | Mn |
| 2-22 | Cl | Cl | CO₂OC₂H₅ | Co |
| 2-23 | CO₂C₂H₅ | CH₃ | Br | Cu |

TABLE 1-3

| Compound | R¹ | R² | R³ | R⁴ |
|---|---|---|---|---|
| 3-1 | $CH_3$ | H | $CH_3$ | $CH_3$ |
| 3-2 | $CH_3$ | $C_2H_5$ | $CH_3$ | 4-methylphenyl |
| 3-3 | $CH_3$ | $CH=CH_2$ | $CH_3$ | $CH_3$ |
| 3-4 | $CH_3$ | $COCH_3$ | $CH_3$ | $CH_3$ |
| 3-5 | $CH_3$ | $CO_2C_2H_5$ | $CH_3$ | CN |
| 3-6 | $CH_3$ | $C_2H_5$ | $CH_3$ | $CH_2OCOCH_3$ |
| 3-7 | H | $O(CH_2)_2OCH(CH_3)_2$ | $CH_3$ | H |
| 3-8 | $CH_3$ | 4-t-Bu-phenyl | H | H |
| 3-9 | $CO_2C_2H_5$ | $CH_3$ | $COCH_3$ | H |
| 3-10 | 5-methyl-oxazol-2-yl | H | H | H |
| 3-11 | $CH_3$ | $SO_3H$ | $CH_3$ | $CH_3$ |
| 3-12 | $CH_3$ | $CONHCH(CH_3)_2$ | $C_2H_5$ | H |
| 3-13 | $CO_2C_2H_5$ | $NHCOC_2H_5$ | $CH_3$ | H |
| 3-14 | $CH_3$ | —NHCO-phenyl | $CH_3$ | $CH_3$ |
| 3-15 | $CH_3$ | —OCO-phenyl | $CH_3$ | $CH_3$ |
| 3-16 | $CO_2C_2H_5$ | $SCH(CH_3)_2$ | $CH_3$ | $CH_3$ |
| 3-17 | COOH | —S-(4-t-Bu-phenyl) | $CH_3$ | H |

| Compound | R⁵ | R⁶ | R⁷ |
|---|---|---|---|
| 3-1 | $CH_3$ | H | $CH_3$ |
| 3-2 | $CH_3$ | $C_2H_5$ | $CH_3$ |
| 3-3 | $CH_3$ | $CH=CH_2$ | $CH_3$ |
| 3-4 | $CH_3$ | $COCH_3$ | $CH_3$ |
| 3-5 | $CH_3$ | $CO_2C_2H_5$ | $CH_3$ |
| 3-6 | $CH_3$ | $C_2H_5$ | $CH_3$ |
| 3-7 | $CH_3$ | $O(CH_2)_2OCH(CH_3)_2$ | H |
| 3-8 | H | 4-t-Bu-phenyl | $CH_3$ |
| 3-9 | $COCH_3$ | $CH_3$ | $CO_2C_2H_5$ |
| 3-10 | $CH_3$ | H | $CH_3$ |
| 3-11 | $CH_3$ | $SO_3H$ | $CH_3$ |
| 3-12 | $C_2H_5$ | $CO_2CH_3$ | $CH_3$ |
| 3-13 | $CH_3$ | $NHCOC_2H_5$ | $CO_2C_2H_5$ |

TABLE 1-3-continued
| | | | | |
|---|---|---|---|---|
| 3-14 | CH$_3$ | —NHCO—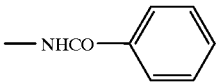 | | CH$_3$ |
| 3-15 | CH$_3$ | —OCO—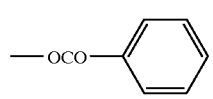 | | CH$_3$ |
| 3-16 | CH$_3$ | SCH(CH$_3$)$_2$ | | CO$_2$C$_2$H$_5$ |
| 3-17 | CH$_3$ | —S—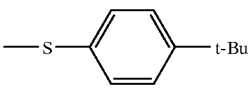—t-Bu | | COOH |
TABLE 1-4
| Compound | R$_1$ | R$^2$ | R$^3$ | R$^4$ | R$^8$ | R$^9$ | R$^{10}$ | R$^{11}$ | R$^7$ | M |
|---|---|---|---|---|---|---|---|---|---|---|
| 4-1 | CH$_3$ | H | CH$_3$ | H | H | H | H | H | 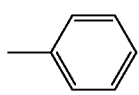 | Co |
| 4-2 | CH$_3$ | H | CH$_3$ | H | H | H | H | H | 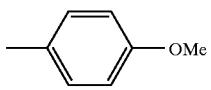—OMe | Co |
| 4-3 | CH$_3$ | H | CH$_3$ | H | H | H | H | H | 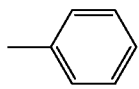 | Zn |
| 4-4 | CH$_3$ | H | CH$_3$ | H | H | H | H | H | —S—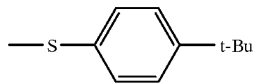—t-Bu | Co |
| 4-5 | CH$_3$ | C$_2$H$_5$ | CH$_3$ | H | H | H | H | H | 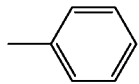 | Co |
| 4-6 | CH$_3$ | C$_2$H$_5$ | CH$_3$ | H | H | H | H | H | 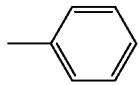 | Zn |
| 4-7 | CH$_3$ | H | CH$_3$ | H | H | H | H | H | —S—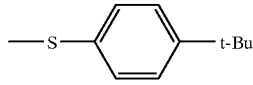—t-Bu | Zn |

TABLE 1-4-continued

| Compound | R¹ | R² | R³ | R⁴ | R⁸ | R⁹ | R¹⁰ | R¹¹ | R⁷ | M |
|---|---|---|---|---|---|---|---|---|---|---|
| 4-8 | $CH_3$ | H | $CH_3$ | CN | H | H | H | H | —S—C₆H₄—t-Bu | Cu |
| 4-9 | $CH_3$ | $C_2H_5$ | $C_2H_5$ | H | H | H | H | H | Br | Cu |
| 4-10 | $CO_2C_2H_5$ | $C_2H_5$ | $C_2H_5$ | H | H | H | H | H | $SC_2H_5$ | Co |
| 4-11 | $CO_2C_2H_5$ | $C_2H_5$ | $C_2H_5$ | H | F | F | F | F | —C₆H₄—Et | Fe |
| 4-12 | $CO_2C_2H_6$ | $n\text{-}C_6H_{17}$ | $C_2H_5$ | H | Br | Br | Br | Br | —S—C₆H₄—t-Bu | Zn |
| 4-13 | $CO_2C_2H_6$ | $n\text{-}C_6H_{13}$ | $CO_2C_2H_5$ | H | H | H | H | H | —C₆H₄—NMe₂ | Zn |

TABLE 1-5

| Compound | R1 | R2 | R3 | R4 | R8 | R9 | R10 | R11 | R7 | M |
|---|---|---|---|---|---|---|---|---|---|---|
| 4-14 | CH$_3$ | C$_2$H$_5$ | *p*-tolyl | H | H | OCH$_3$ | OCH$_3$ | H | *p*-(t-Bu)-phenyl | Ni |
| 4-15 | CH$_3$ | *p*-tolyl | *p*-tolyl | H | H | H | H | H | CH$_3$ | Co |
| 4-16 | CH$_3$ | COCH$_3$ | *p*-tolyl | CN | H | H | H | H | C$_2$H$_5$ | Ni |
| 4-17 | CH$_3$ | (CH$_2$)$_2$CO$_2$CH$_3$ | CH$_3$ | CN | H | OC$_2$H$_5$ | OC$_2$H$_5$ | H | phenyl | Cu |
| 4-18 | –CH$_2$-(2,4,6-Me$_3$-phenyl) | H | H | CN | H | OCH$_3$ | OCH$_3$ | H | phenyl | Ni |
| 4-19 | CH$_3$ | CO$_2$CH$_2$CO$_2$CH$_3$ | CH$_3$ | H | H | H | H | H | Cl | Zn |
| 4-20 | Br | CH$_3$ | CO$_2$C$_2$H$_5$ | H | OCH$_3$ | OCH$_3$ | OCH$_3$ | OCH$_3$ | phenyl | Fe |

TABLE 1-5-continued

| Compound | $R^1$ | $R^2$ | $R^3$ | $R^4$ | $R^8$ | $R^9$ | $R^{10}$ | $R^{11}$ | $R^7$ | M |
|---|---|---|---|---|---|---|---|---|---|---|
| 4-21 | $OCH_3$ | $CH_3$ | $C_2H_5$ | H | H | H | Cl | H | 4-methylphenyl | Fe |
| 4-22 | 2-methyl-1H-pyrrol-yl | H | $OCH_3$ | H | H | H | H | H | 4-(t-Bu)phenyl-S- | Cu |
| 4-23 | $CO_2C_2H_5$ | Cl | Cl | CN | H | H | 4-(t-Bu)phenyl-S- | H | H | Ni |
| 4-24 | $CH_3$ | $n\text{-}C_4H_9$ | H | CN | H | phenyl | 4-methylphenyl | H | H | Co |
| 4-25 | $CH_3$ | $O(CH_2)_3OC(CH_3)_3$ | $CH_3$ | H | H | H | $SCH_3$ | H | 4-ethylphenyl | Co |

TABLE 1-6

| Compound | R¹ | R² | R³ | R⁴ | R⁸ | R⁹ |
|---|---|---|---|---|---|---|
| 4-26 | CH₃ | -C₆H₄-t-Bu (para) | H | H | H | OCH₃ |
| 4-27 | CO₂C₂H₅ | CH₃ | CO₂CH₃ | H | H | -C₆H₅ |
| 4-28 | 5-methyloxazolyl | SO₃H | H | CN | H | H |
| 4-29 | CH₃ | SO₃H | CH₃ | H | H | H |
| 4-30 | CH₃ | CONHCH(CH₃)₂ | H | H | H | H |
| 4-31 | CO₂C₂H₅ | NHCOC₂H₅ | CH₃ | H | H | H |
| 4-32 | CH₃ | -NHCO-C₆H₅ | CH₃ | H | H | H |
| 4-33 | CH₃ | -OCO-C₆H₅ | CH₃ | CN | H | OC₂H₅ |
| 4-34 | CO₂C₂H₅ | SC(CH₃)₃ | CH₃ | CN | H | H |
| 4-35 | CO₂H | -S-C₆H₄-t-Bu (para) | CH₃ | H | F | F |
| 4-35 | CH₃ | NO₂ | CH₃ | H | H | H |
| 4-37 | CH₃ | CN | H | H | H | H |
| 4-38 | OH | CONHCH₂OCH₃ | CH₃ | CN | H | H |

| Compound | R¹⁰ | R¹¹ | R⁷ | M |
|---|---|---|---|---|
| 4-26 | OCH₃ | H | CH₃ | Zn |
| 4-27 | -C₆H₅ | H | CO₂CH₃ | Co |
| 4-28 | Cl | H | CO₂CH₃ | Zn |
| 4-29 | H | H | OC₂H₅ | Zn |
| 4-30 | H | H | CN | Pd |
| 4-31 | H | H | NHC₂H₅ | Co |
| 4-32 | H | H | -C₆H₅ | Pd |
| 4-33 | OC₂H₅ | H | N(CH₃)₂ | Mn |
| 4-34 | H | H | -C₆H₄-Et (para) | Ni |

TABLE 1-6-continued
| | | | | |
|---|---|---|---|---|
| 4-35 | F | F | 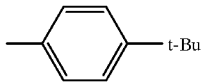 | Co |
| 4-35 | H | H | 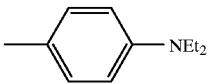 | Zn |
| 4-37 | H | H | 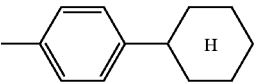 | Mn |
| 4-38 | H | H | 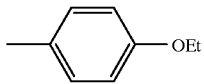 | Ni |

TABLE 1-7

| Compound | R$^1$ | R$^2$ | R$^3$ | R$^4$ | R$^8$ | R$^9$ | R$^{10}$ | R$^{11}$ | R$^7$ | M |
|---|---|---|---|---|---|---|---|---|---|---|
| 4-39 | NH$_2$ | C$_2$H$_5$ | CH$_3$ | CN | H | H | Cl | H |  p-tolyl-NEt$_2$ | Mn |
| 4-40 | C$_2$F$_5$ | CON(CH$_2$OCH$_3$)$_2$ | C$_2$H$_5$ | H | H | H | H | H | CO$_2$C$_2$H$_5$ | Co |
| 4-41 | CH$_2$OCH$_3$ | C$_2$H$_5$ | CH$_3$ | H | H | H | H | H | CO$_2$C$_2$H$_5$ | Fe |
| 4-42 |  4-t-Bu-phenoxy | C$_2$H$_5$ | CH$_3$ | H | Cl | Cl | Cl | Cl |  tolyl | Co |
| 4-43 | CH$_3$ |  —CO$_2$— phenyl | H | H | H | H | H | H | Br | Fe |
| 4-44 | CH$_3$ |  —CO$_2$CH$_2$CH$_3$ | CH$_3$ | CN | H | H | H | H | C(CH$_3$)$_3$ | Fe |
| 4-45 | H |  —OCH$_2$-p-tolyl | H | H | H | OCH$_3$ | OCH$_3$ | H | CH$_3$ | Cu |
| 4-46 | H | CH=CH$_2$ | H | H | H | H | H | H |  phenyl | Ni |
| 4-47 | CH$_3$ | C$_2$H$_5$ | C$_2$H$_5$ | H | H | H | H | H |  2,5-di-i-Pr-tolyl | Cu |

TABLE 1-7-continued

| Compound | R¹ | R² | R³ | R⁴ | R⁸ | R⁹ | R¹⁰ | R¹¹ | R⁷ | M |
|---|---|---|---|---|---|---|---|---|---|---|
| 4-48 | CH₃ | C₂H₅ | CH₃ | H | H | H | H | H | 2,4-di(i-Pr)-phenyl (methyl) | Co |
| 4-49 | CH₃ | CH₃ | OCH₃ | H | H | H | H | H | phenyl | Co |
| 4-50 | CH₃ | C₂H₅ | CH₃ | H | H | H | H | H | 4-N(n-Bu)₂-phenyl (methyl) | Zn |
| 4-51 | phenyl(methyl) | H | phenyl(methyl) | H | H | H | H | H | 2,4-di(i-Pr)-phenyl(methyl) | Cu |

TABLE 1-8
| Compound | R¹ | R² | R³ | R⁴ | R⁸ | R⁹ | R¹⁰ | R¹¹ | R⁷ |
|---|---|---|---|---|---|---|---|---|---|
| 5-1 | CH₃ | H | CH₃ | H | H | H | H | H | 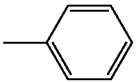 |
| 5-2 | CH₃ | H | CH₃ | H | H | H | H | H | 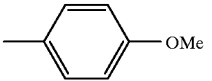 —OMe |
| 5-3 | CH₃ | H | CH₃ | H | H | H | H | H | —S—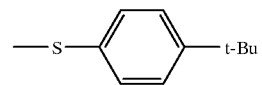—t-Bu |
| 5-4 | CH₃ | C₂H₅ | CH₃ | H | H | H | H | H | 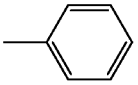 |
| 5-5 | CH₃ | C₂H₅ | CH₃ | CN | H | H | H | H | Cl |
| 5-6 | CH₃ | C₂H₅ | C₂H₅ | H | H | H | H | H | Br |
| 5-7 | CH₃ | C₂H₅ | 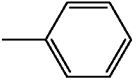 | H | H | H | H | H | 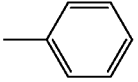 |
| 5-8 | CH₃ | 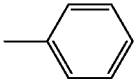 | 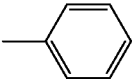 | H | H | H | H | H | SCH₃ |
| 5-9 | CH₃ | 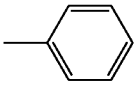 | 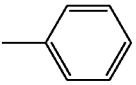 | H | H | H | H | H | Cl |
| 5-10 | CH₃ | C₂H₅ | 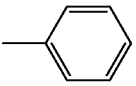 | H | H | H | H | H | SC₂H₅ |
| 5-11 | CH₃ | COCH₃ | 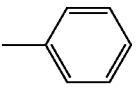 | CN | H | F | H | H | 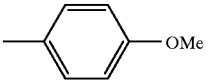—OMe |
| 5-12 | CH₃ | COCH₃ | 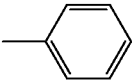 | H | H | H | H | H | 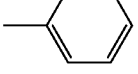 |
60

TABLE 1-9

| Compound | R¹ | R² | R³ | R⁴ | R⁸ | R⁹ |
|---|---|---|---|---|---|---|
| 5-13 | -CH₂-(2,4,6-trimethylphenyl) | H | H | H | H | H |
| 5-14 | CH₃ | CO₂C₂H₅ | CH₃ | H | H | H |
| 5-15 | CH₃ | CO₂C₂H₅ | CH₃ | H | H | H |
| 5-16 | Br | CH₃ | CO₂C₂H₅ | CN | H | H |
| 5-17 | OCH₃ | CH₃ | C₂H₅ | H | H | H |
| 5-18 | OCH₃ | CH₃ | C₂H₅ | CN | F | F |
| 5-19 | 2-(5-methyl-1H-pyrrolyl) | H | OCH₃ | H | H | H |
| 5-20 | CO₂C₂H₅ | Cl | Cl | H | H | H |
| 5-21 | CH₃ | 4-t-Bu-phenyl | H | H | H | H |
| 5-22 | CH₃ | 4-t-Bu-phenyl | H | H | H | OCH₃ |
| 5-23 | CH₃ | CONHCH(CH₃)₂CH₃ | H | H | Br | Br |
| 5-24 | CO₂C₂H₅ | NHCOC₂H₅ | CH₃ | H | H | OC₂H₅ |

| Compound | R¹⁰ | R¹¹ | R⁷ |
|---|---|---|---|
| 5-13 | Cl | H | 4-Et-phenyl |
| 5-14 | Cl | H | 4-t-Bu-phenyl |
| 5-15 | H | H | CH₃ |
| 5-16 | SCH₃ | H | phenyl |
| 5-17 | -S-(4-t-Bu-phenyl) | H | H |
| 5-18 | F | F | H |
| 5-19 | H | H | 4-NMe₂-phenyl |

TABLE 1-9-continued
| | | | |
|---|---|---|---|
| 5-20 | H | H | 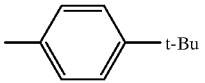 |
| 5-21 | H | H | 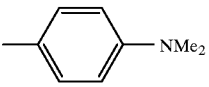 |
| 5-22 | OCH$_3$ | H | CH$_3$ |
| 5-23 | Br | Br | Br |
| 5-24 | OC$_2$H$_5$ | H | CH$_3$ |

TABLE 1-10

| Compound | R¹ | R² | R³ | R⁴ | R⁸ | R⁹ | R¹⁰ | R¹¹ | R⁷ |
|---|---|---|---|---|---|---|---|---|---|
| 5-25 | CO₂C₂H₅ | —C₆H₄—CONH— | CH₃ | CN | SC₂H₅ | SC₂H₅ | SC₂H₅ | SC₂H₅ | OH |
| 5-26 | CH₃ | —C₆H₄—HNCO— | CH₃ | CN | H | p-CH₃-C₆H₄— | p-CH₃-C₆H₄— | H | p-Et-C₆H₄— |
| 5-27 | CO₂C₂H₅ | SC(CH₃)₃ | CH₃ | H | OCH₃ | OCH₃ | OCH₃ | OCH₃ | m-CH₃-C₆H₄— |
| 5-28 | C₂H₅ | CO₂CH=CH₂ | C₂H₅ | H | H | H | H | H | CO₂CH₃ |
| 5-29 | CH₃ | CON(C₂H₅)₂ | C₂H₅ | H | H | H | H | H | OC₂H₅ |
| 5-30 | CON(CH₂OH)₂ | n-C₈H₁₇ | C₂H₅ | H | H | H | H | H | CN |
| 5-31 | CO₂C₂H₅ | —C₆H₄—COO— | CO₂C₂H₅ | CN | H | H | OCH₃ | H | NHCH₃ |
| 5-32 | CH₃ | NO₂ | CH₃ | H | H | OCH₃ | OCH₃ | H | NHCH₃ |
| 5-33 | NH₂ | C₂H₅ | CH₃ | H | F | F | F | F | NO₂ |
| 5-34 | CONHCH₂OH | C₂H₅ | C₂H₅ | H | H | H | CO₂H | H | p-t-Bu-C₆H₄—S— |
| 5-35 | H | —C₆H₄—CO₂CH₂— | H | H | H | H | Cl | H | OCH₂OC₂H₅ |

TABLE 1-10-continued

| Compound | R¹ | R² | R³ | R⁴ | R⁸ | R⁹ | R¹⁰ | R¹¹ | R⁷ |
|---|---|---|---|---|---|---|---|---|---|
| 5-36 | CH₃ | CH=CH₂ | CH₃ | H | H | H | -S-C₆H₄-t-Bu (para) | H | C₆H₄-CH₃ (tolyl) |
| 5-37 | CH₃ | C₂H₅ | CH₃ | H | H | H | H | H | 2-i-Pr-4-methyl-5-i-Pr phenyl |

TABLE 1-11

| Compound | R¹ | R¹¹ | R¹⁰ | R⁹ | R⁸ | R⁴ | R⁸' | R⁹' |
|---|---|---|---|---|---|---|---|---|
| 11-1 | C(CH$_3$)$_3$ | H | H | H | H | H | H | H |
| 11-2 | phenyl | —CH=CH—CH=CH— | | H | H | H | H | H |
| 11-3 | C(CH$_3$)$_3$ | C(CH$_3$)$_3$ | H | H | H | H | H | H |
| 11-4 | 4-OMe-phenyl | —CH=CH—CH=CH— | | H | H | H | H | H |
| 11-5 | C(CH$_3$)$_3$ | H | H | H | H | H | H | H |
| 11-6 | phenyl | —CH=CH—CH=CH— | | H | H | H | H | H |
| 11-7 | C(CH$_3$)$_3$ | C(CH$_3$)$_3$ | H | H | H | H | H | H |
| 11-8 | 4-OMe-phenyl | —CH=CH—CH=CH— | | H | H | H | H | H |
| 11-9 | C(CH$_3$)$_3$ | H | H | H | H | H | H | H |
| 11-10 | phenyl | —CH=CH—CH=CH— | | H | H | H | H | H |

| Compound | R¹⁰' | R¹¹' | R⁷ | M |
|---|---|---|---|---|
| 11-1 | H | H | C(CH$_3$)$_3$ | Zn |
| 11-2 | —CH=CH—CH=CH— | | phenyl | Zn |
| 11-3 | H | OCH$_3$ | C(CH$_3$)$_3$ | Zn |
| 11-4 | —CH=CH—CH=CH— | | 4-OMe-phenyl | Zn |
| 11-5 | H | H | C(CH$_3$)$_3$ | Cu |
| 11-6 | —CH=CH—CH=CH— | | phenyl | Cu |
| 11-7 | H | OCH$_3$ | C(CH$_3$)$_3$ | Fe |
| 11-8 | —CH=CH—CH=CH— | | 4-OMe-phenyl | Co |
| 11-9 | H | H | C(CH$_3$)$_3$ | Ni |

TABLE 1-11-continued

| | | | |
|---|---|---|---|
| 11-10 | —CH=CH—CH=CH— | 4-methylphenyl | Pd |

TABLE 1-12

| Compound | $R^1$ | $R^{11}$ | $R^{10}$ | $R^9$ | $R^8$ | $R^4$ | $R^{8'}$ |
|---|---|---|---|---|---|---|---|
| 12-1 | $C(CH_3)_3$ | H | H | H | H | H | H |
| 12-2 | 4-methylphenyl | —CH=CH—CH=CH— | | H | H | H | H |
| 12-3 | $C(CH_3)_3$ | $C(CH_3)_3$ | H | H | H | H | H |
| 12-4 | 4-methoxyphenyl | —CH=CH—CH=CH— | | H | H | H | H |
| 12-5 | $C(CH_3)_3$ | $OCH_3$ | H | $CH_2OCOCH_3$ | H | H | H |
| 12-6 | $CH_3$ | $CONHCH(CH_3)_2$ | H | Br | H | H | H |
| 12-7 | $CH_3$ | $SCH(CH_3)_2$ | H | $NHCOC_2H_5$ | H | H | H |
| 12-8 | 4-t-Bu-thiophenyl(SMe) | —CH=CH—CH=CH— | | $COCH_3$ | H | H | H |
| 12-9 | $C(CH_3)_3$ | $C(CH_3)_3$ | —OCO-phenyl | COOH | H | H | H |
| 12-10 | $C(CH_3)_3$ | 2-pyrrolyl (NH) | H | $CH_2OCOCH_3$ | H | H | H |

| Compound | $R^{9'}$ | $R^{10'}$ | $R^{11'}$ | $R^7$ |
|---|---|---|---|---|
| 12-1 | H | H | H | $C(CH_3)_3$ |
| 12-2 | H | —CH=CH—CH=CH— | | 4-methylphenyl |
| 12-3 | H | H | $OCH_3$ | $C(CH_3)_3$ |
| 12-4 | H | —CH=CH—CH=CH— | | 4-methoxyphenyl |
| 12-5 | $CH_2OCOCH_3$ | H | $OCH_3$ | $C(CH_3)_3$ |
| 12-6 | Br | H | $CONHCH(CH_3)_2$ | $CH_3$ |
| 12-7 | $NHCOC_2H_5$ | H | $SCH(CH_3)_2$ | $CH_3$ |

TABLE 1-12-continued

| | | | |
|---|---|---|---|
| 12-8 | COCH$_3$ | —CH=CH—CH=CH— | —S—⟨C$_6$H$_4$⟩—t-Bu |
| 12-9 | COOH | —OCO—⟨C$_6$H$_5$⟩ | C(CH$_3$)$_3$ ... C(CH$_3$)$_3$ |
| 12-10 | CH$_2$OCOCH$_3$ | H | (pyrrole-NH) ... C(CH$_3$)$_3$ |

The constitution of the present invention will be described in detail as follows.

Figure 2:
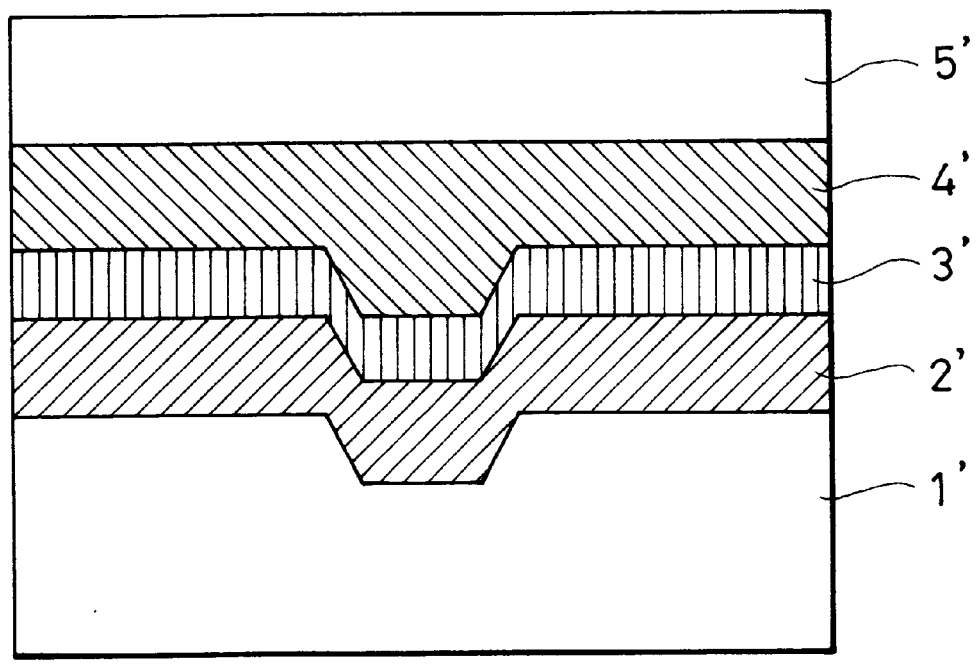
FIG. 2 is a sectional view illustrating a layer constitution of an optical recording medium of the present invention.

The optical recording medium denotes both of an optical ROM medium for reproduction alone in which information is beforehand recorded, and an optical recording medium by which the information can be recorded and then reproduced. However, reference will here be made to the latter optical recording medium as a suitable example by which the information can be recorded and reproduced, particularly the optical recording medium having a recording layer and a reflective layer on a substrate. As shown in FIG. 1, this optical recording medium has a four-layer structure in which the substrate, the recording layer, the reflective layer and a protective layer are laminated in turn, or such a laminated structure as shown in FIG. 2. That is to say, a recording layer 2' is formed on a substrate 1', and a reflective layer 3' is closely formed thereon. Furthermore, a substrate 5' is stuck on the reflective layer 3' via an adhesive layer 4'. However, another layer may be formed under or on the recording layer 2', and still another layer may be formed on the reflective layer.

A material for the substrate should fundamentally be transparent for a wavelength of a record light and a reproduction light. Utilizable examples of such a material include polymeric materials such as polycarbonate resins, vinyl chloride resins, acrylic resins such as polymethyl methacrylate, polystyrene resins and epoxy resins as well as inorganic materials such as glass. The substrate material is molded into a disc substrate by injection molding or the like. If necessary, guide grooves or pits may be formed on the surface of the substrate. Such guide grooves or pits are preferably formed at the time of the molding of the substrate, but they can also be formed by the use of an ultraviolet curing resin layer on the substrate. In the case that the optical recording medium is used in the form of a CD, the substrate is a disc having a thickness of about 1.2 mm and a diameter of about 80 to 120 mm, and having a hole of about 15 mm in diameter in its center.

In the present invention, the recording layer is formed on the substrate, and the recording layer of the present invention contains the chelate compound of the dipyrromethene compound represented by the general formula (1) and the metal ion. The maximum absorption $\lambda_{max}$ of the chelate compound is present in 450 to 630 nm. In particular, the recording layer is required to have an optical constant suitable for a record and reproduction laser wavelength selected in the range of 520 to 690 nm.

The optical constant is represented by a complex index of refraction (n+iκ) wherein n and κ are coefficients of a real number and an imaginary number, respectively, and herein, n and κ mean an ordinary refractive index and an extinction coefficient, respectively. In general, an organic dye has a feature that the refractive index n and the extinction coefficient κ largely change to a wavelength λ. In view of this feature, the organic dye having the preferable optical constant suitable for the desired laser wavelength should be selected to form the recording layer, whereby the medium having a high reflectance and a good sensitivity can be obtained.

According to the present invention, the optical constant necessary for the recording layer is such that, at the above-mentioned wavelength of the laser light, n is 1.8 or more and κ is in the range of 0.04 to 0.40, and preferably n is 2.0 or more and κ is in the range of 0.04 to 0.20. If n is less than 1.8, the reflectance and the signal modulation amplitude necessary for a correct signal read may not be obtained, and if κ is more than 0.40, the reflectance is low, so that a good regenerative signal may not be obtained and in addition, the signal is liable to change by a regenerative light. Hence, the recording layer having such an extinction coefficient κ may be not practical. In view of this feature, the organic dye having the preferable optical constant suitable for the desired laser wavelength should be selected to form the recording layer, whereby the medium having a high reflectance and a good sensitivity can be obtained. The chelate compound of the dipyrromethene compound represented by the general formula (1) with a metal of the present invention has a higher absorption coefficient as compared with a conventional organic dye and can optionally select an absorption wavelength section by the choice of a substituent. Therefore, it is an extremely useful compound which can satisfy the optical constant (n is 1.8 or more and κ is in the range of 0.04 to 0.40, and preferably n is 2.0 or more and κ is in the range of 0.04 to 0.20) necessary for the recording layer at the above-mentioned wavelength of the laser light.

In the case that the optical recording medium of the present invention is reproduced by the laser light selected in the range of 520 to 690 nm, the reproduction is basically possible when the reflectance is 20% or more, but it is preferred that the reflectance is 30% or more.

Furthermore, for the improvement of record characteristics and the like, the recording layer may be mixed with a dye, other than mentioned above, having a maximum absorption in the wavelength range of 450 to 630 nm and a large refractive index in the range of 520 to 690 nm. Typical examples of such a dye include cyanine dyes, squalirium dyes, naphthoquinone dyes, anthraquinone dyes, porphyrin dyes, tetrapyraporphyrazine dyes, indophenol dyes, pyrylium dyes, thiopyrylium dyes, azulenium dyes, triphenylmethane dyes, xanthene dyes, indanthrene dyes, indigo dyes, thioindigo dyes, merocyanine dyes, thiazine dyes, acridine dyes and oxazine dyes, and they may be used singly or in the form of a mixture of two or more thereof. A mixing ratio of the dye to be used is in the range of about 0.1 to 30%.

In addition, when κ is small for the record and regenerative laser wavelength of the chelate compound of the dipyrromethene compound represented by the general formula (1) with metal selected from the range of 520 to 690 nm, the recording layer may be mixed with a light absorbing compound having a maximum absorption in the wavelength range of 600 to 900 nm for the sake of the improvement of the record characteristics and the like. Typical examples of the light absorbing compound include cyanine dyes, squalirium dyes, naphthoquinone dyes, anthraquinone dyes, porphyrin dyes, tetrapyraporphirazine dyes, indophenol dyes, pyrylium dyes, thiopyrylium dyes, azulenium dyes, triphenylmethane dyes, xanthene dyes, indanthrene dyes, indigo dyes, thioindigo dyes, merocyanine dyes, thiazine dyes, acridine dyes, oxazine dyes, phthalocyanine dyes and naphthalocyanine dyes, and they may be used singly or in the form of a mixture of two or more thereof. A mixing ratio of the dye to be used is in the range of about 0.1 to 30%.

Prior to the formation of the recording layer, the above-mentioned dye can be mixed with any of a quencher, a dye decomposition accelerator, an ultraviolet absorber, an adhesive and the like, or alternatively a compound having such an effect can also be introduced into the dye as a substituent.

Typical examples of the quencher include metal complexes of acetylacetonates, bisdithiols such as bisdithio-α-diketones and bisphenyldithiols, thiocatechols, salicylaldehydeoximes, thiobisphenolates and the like. In addition, amines are suitable.

Examples of the dye decomposition accelerator include metallic compounds such as metallic anti-knock agents, metallocene compounds and metal complexes of acetylacetonates.

Additionally, if necessary, a binder, a leveling agent and an anti-foaming agent can also be used together. Examples of the preferable binder include polyvinyl alcohol, polyvinyl pyrrolidone, nitrocellulose, cellulose acetate, ketone resins, acrylic resins, polystyrene resins, urethane resins, polyvinyl butyral, polycarbonates and polyolefins.

Prior to the formation of the recording layer on the substrate, a layer comprising an inorganic substance and a polymer may be formed on the substrate in order to improve the solvent resistance and the reflectance of the substrate as well as the record sensitivity.

Here, the content of the metal chelate of the dipyrromethene compound represented by the general formula (1) in the recording layer is 30% or more, preferably 60% or more. It is also preferred that the content is substantially 100%.

Examples of a technique for forming the recording layer include coating methods such as spin-coating, spraying, casting and an immersion, a sputtering process, a chemical vapor deposition method and a vacuum vapor deposition method, but the spin-coating method is preferable because of being simple and easy.

In the case that a coating technique such as the spin-coating method is used, there can be used a coating solution prepared by dissolving or dispersing the metal chelate of the dipyrromethene compound represented by the general formula (1) in a solvent so that the content of the metal chelate may be in the range of 1 to 40% by weight, preferably 3 to 30% by weight. In this case, it is preferable to select the solvent which does not damage the substrate. Examples of the solvent include alcohol solvents such as methanol, ethanol, isopropyl alcohol, octafluoropentanol, allyl alcohol, methyl cellosolve, ethyl cellosolve and tetrafluoropropanol, aliphatic and alicyclic hydrocarbon solvents such as hexane, heptane, octane, decane, cyclohexane, methylcyclohexane, ethylcyclohexane and dimethylcyclohexane, aromatic hydrocarbon solvents such as toluene, xylene and benzene, hydrocarbon halide solvents such as carbon tetrachloride, chloroform, tetrachloroethane and dibromoethane, ether solvents such as diethyl ether, dibutyl ether, diisopropyl ether and dioxane, ketone solvents such as acetone and 3-hydroxy-3-methyl-2-butanone, ester solvents such as ethyl acetate and methyl lactate, and water. They may be used singly or in the form of a mixture of two or more thereof.

If necessary, the dye for the recording layer can be dispersed in a polymeric thin film or the like.

In the case that the solvent which does not damage the substrate cannot be selected, the sputtering process, the chemical vapor deposition method or the vacuum vapor deposition method is effective.

No particular restriction is put on the thickness of the recording layer, but it is preferably in the range of 50 to 300 nm. If the thickness of the recording layer is less than 50 nm, heat diffusion is large, so that the record may not be done, or strain may occur on a record signal and a signal amplitude may decrease. On the contrary, if the thickness of the dye layer is more than 300 nm, the reflectance may become insufficient and reproducing signal characteristics may deteriorate.

Next, a reflective layer having a thickness of preferably 50 to 300 nm is formed on the recording layer. As a material for the reflective layer, substances having the sufficiently high reflectance at the wavelength of the regenerative light, for example, metals such as Au, Al, Ag, Cu, Ti, Cr, Ni, Pt, Ta, Cr and Pd can be used singly or in the form of an alloy thereof. Above all, Au, Al and Ag are suitable as the materials for the reflective layer, because of having the high reflectance. As the material for the reflective layer, substances other than mentioned above can also be used, and examples of such substances include metals and semimetals such as Mg, Se, Hf, V, Nb, Ru, W, Mn, Re, Fe, Co, Rh, Ir, Zn, Cd, Ga, In, Si, Ge, Te, Pb, Po, Sn and Bi. The material containing Au as the main component is suitable, because the refractive layer having the high reflectance can easily be obtained. Here, the term "main component" means a component which is contained in a ratio of 50% or more. It is also possible that a multilayer prepared by alternately laminating a thin film having a low refractive index and a thin film having a high refractive index in which the films are made from materials other than the metals can also be used as the reflective layer.

Examples of a technique for forming the reflective layer include a sputtering process, an ion plating method, a chemical vapor deposition method and a vacuum vapor deposition method. In addition, for the improvement of properties such as reflectance, record characteristics and adhesive properties, an intermediate layer or an adhesive layer of a known inorganic or organic material can be formed on the substrate or under the reflective layer.

Furthermore, no particular restriction is put on a material for the protective layer on the reflective layer, so long as it can protect the reflective layer from an external force.

Examples of the organic material for the protective layer include thermoplastic resins, thermosetting resins, electron radiation curing resins and UW curing resins. Moreover, examples of the inorganic material for the protective layer include $SiO_2$, $Si_3N_4$, $MgF_2$ and $SnO_2$. The thermoplastic resin or the thermosetting resin can be dissolved in a suitable solvent, and the resulting coating solution is applied and then dried, whereby the protective layer can be formed. The UV curing resin can directly be used as it is, or it can be dissolved in a suitable solvent to prepare a coating solution, and this coating solution is applied and then irradiated with UV light to cure it, whereby the protective layer can be formed. Examples of the usable UV curing resin include acrylate resins such as urethane acrylate, epoxy acrylate and polyester acrylate. These materials may be used singly or in the state of a mixture thereof, and this kind of resin may also be used in the form of a singly layer or a multilayer.

Examples of a technique for forming the protective layer include coating methods such as spin-coating and casting, a sputtering process and a chemical vapor deposition method, as in the case of the formation of the recording layer, but above all, the spin-coating method is preferable.

The thickness of the protective layer is usually in the range of 0.1 to 100 µm, but in the present invention, it is in the range of 3 to 30 µm, preferably 5 to 20 µm.

On the protective layer, a label or the like can further be printed.

In addition, there may be employed a means of laminating the protective sheet or the substrate on the surface of the reflective layer, or another means of laminating the two optical record media so that the reflective layers may come in contact with each other. For the purpose of protecting the surface or preventing the deposition of dust or the like, an ultraviolet curing resin layer, an inorganic thin film or the like may be formed on the mirror surface of the substrate.

No particular restriction is put on the laser having a wavelength of 520 to 690 nm referred to in the present invention, and examples of such a laser include a dye laser capable of selecting the wavelength in the wide range of visible light, a helium neon laser having a wavelength of 633 nm, a high-output semiconductor laser having a wavelength of about 680, 650 or 635 nm which has been developed of late, and a high-frequency conversion YAG laser having a wavelength of 532 nm. In the present invention, the high-density record and reproduction is possible at one wavelength or plural wavelengths selected from them.

Next, the present invention will be described in detail with reference to examples, but the scope of the present invention should not be limited to these examples.

EXAMPLE 1

0.2 g of a compound (2-1) mentioned in Table 1 among metal chelate of dipyrromethene compounds represented by formula (1) was dissolved in 10 ml of dimethylcyclohexane to prepare a dye solution. As a substrate, there was used a disc made of a polycarbonate resin and having a spiral pre-groove (track pitch=0.8 µm) thereon, a diameter of 120 mm and a thickness of 1.2 mm.

This substrate was spin-coated with the dye solution at a rotational frequency of 1500 rpm, and then dried at 70° C. for 3 hours to form a recording layer. With regard to this recording layer, its maximum absorption was present at 505 nm, and its optical constant was such that at 680 nm, n was 2.1 and κ was 0.04; at 650 nm, n was 2.2 and κ was 0.05; and at 635 nm, n was 2.3 and κ was 0.07.

Next, Au was sputtered on this recording layer by the use of a sputtering device (CDI-900) made by Bulzers Co., Ltd. to form a reflective layer having a thickness of 100 nm. As a sputtering gas, an argon gas was used. Sputtering conditions were that a sputtering power was 2.5 kW and a sputtering pressure was $1.0 \times 10^{-2}$ Torr.

In addition, the reflective layer was spin-coated with an ultraviolet curing resin SD-17 (made by Dainippon Ink & Chemicals, Inc.), and then irradiated with ultraviolet light to form a protective layer having a thickness of 6 µm, thereby preparing an optical recording medium.

Furthermore, recording was carried out on the optical recording medium at a linear velocity of 3.5 m/sec under a laser power of 8 mW by the use of an optical disc evaluation device (DDU-1000) equipped with a semiconductor laser head having a lens numerical aperture of 0.6 at a wavelength of 635 nm and made by Pulstech Industry Co., Ltd. and an EFM encoder made by KENWOOD Co., Ltd. so that a shortest pit length might be 0.44 µm. After the recording, signals were reproduced by the use of an evaluation device equipped with a red semiconductor laser head (lens numerical aperture=0.6) of 650 nm and 635 nm to measure a reflectance, an error rate and a modulation amplitude. As a result, all of the measured values were good.

Next, recording was done at a linear velocity of 1.4 m/sec under a laser power of 10 mW by the use of the optical disc evaluation device (DDU-1000) equipped with the 680 nm semiconductor laser head and made by Pulstech Industry Co., Ltd. and the EEM encoder made by KENWOOD Co., Ltd. so that a shortest pit length might be 0.60 µm. Afterward, signals were reproduced from the recorded medium by the use of the optical disc evaluation device (DDU-1000) equipped with the red semiconductor laser head of 680 nm, 650 and 635 nm to measure a reflectance, an error rate and a modulation amplitude. As a result, all of the measured values were good.

As described above, the recording and the reproduction could successfully be carried out on this medium by a plurality of laser wavelengths.

In this connection, the error rate was measured by the use of a CD decoder (DR3552) made by KENWOOD Co., Ltd., and the modulation amplitude was calculated in accordance with the following equation:

$$\text{Modulation degree} = \frac{\left(\begin{array}{c}\text{Maximum strength}\\ \text{of signal}\end{array}\right) - \left(\begin{array}{c}\text{Minimum strength}\\ \text{of signal}\end{array}\right)}{\left(\begin{array}{c}\text{Maximum strength}\\ \text{of signal}\end{array}\right)}$$

EXAMPLE 2

The same procedure as in Example 1 was conducted except that a disc made of a polycarbonate resin and provided with a spiral pre-groove (track pitch=0.8 µm) thereon and having a diameter of 120 mm and a thickness of 0.6 mm was used as a substrate, thereby forming a recording layer and a reflective layer thereon.

In addition, the reflective layer was spin-coated with an ultraviolet curing resin SD-301 (made by Dainippon Ink & Chemicals, Inc.), and another disc substrate made by the polycarbonate resin and having a diameter of 120 mm and a thickness of 0.6 mm was then superposed thereon. Afterward, these layers were irradiated with ultraviolet light to form a laminated optical recording medium.

Next, recording was carried out on the thus formed medium by the use of an optical disc evaluation device (DDU-1000) made by Pulstech Industry Co., Ltd. and an EFM encoder made by KENWOOD Co., Ltd. in the same manner as in Example 1 except that the optical disc evaluation device was equipped with a semiconductor laser head of 635 nm corresponding to a thickness of 0.6 mm. After the recording, signals were reproduced by the use of an evaluation device equipped with a red semiconductor laser head of 650 nm and 635 nm to measure a reflectance, an error rate and a modulation amplitude. As a result, all of the measured values were good.

EXAMPLE 3

The same procedure as in Example 2 was conducted except that a disc made of a polycarbonate resin and provided with a spiral pre-groove (track pitch=1.2 μm) thereon and having a diameter of 120 mm and a thickness of 0.6 mm was used as a substrate, thereby forming an optical recording medium.

Next, recording was carried out on the thus formed medium by the use of an optical disc evaluation device (DDU-1000) made by Pulstech Industry Co., Ltd. and an EF encoder made by KENWOOD Co., Ltd. in the same manner as in Example 1 except that the optical disc evaluation device was equipped with a semiconductor laser head of 635 nm corresponding to a thickness of 0.6 mm. After the recording, signals were reproduced by the use of an evaluation device equipped with a red semiconductor laser head of 650 nm and 635 nm to measure a reflectance, an error rate and a modulation amplitude. As a result, all of the measured values were good.

EXAMPLE 4

The same procedure as in Example 2 was conducted except that a disc made of a polycarbonate resin and provided with a spiral pre-groove (track pitch=0.7 μm) thereon and having a diameter of 120 mm and a thickness of 0.6 mm was used as a substrate, thereby forming an optical recording medium.

Next, recording was carried out on the thus formed medium by the use of an optical disc evaluation device (DDU-1000) made by Pulstech Industry Co., Ltd. and an EFM encoder made by KENWOOD Co., Ltd. in the same manner as in Example 1 except that the optical disc evaluation device was equipped with a semiconductor laser head of 635 nm corresponding to a thickness of 0.6 mm. After the recording, signals were reproduced by the use of an evaluation device equipped with a red semiconductor laser head of 650 nm and 635 nm to measure a reflectance, an error rate and a modulation amplitude. As a result, all of the measured values were good.

EXAMPLE 5

The same procedure as in Example 2 was conducted except that a dipyrromethene metal chelate compound (3-1) mentioned in Table 1 and diacetone alcohol as a coating solvent were used and a disc made of a polycarbonate resin and provided with a spiral pre-groove (track pitch=0.53 μm) thereon and having a diameter of 120 mm and a thickness of 0.6 mm was used as a substrate, thereby forming an optical recording medium. With regard to this recording layer, its maximum absorption was present at 520 nm, and its optical constant was such that at 532 nm, n was 2.4 and κ was 0.15.

Next, recording was carried out on the thus formed medium at a linear velocity of 3.8 m/sec under a laser power of 7 mW by the use of an optical disc evaluation device equipped with a YAG high-frequency conversion laser head of 532 nm corresponding to a thickness of 0.6 mm and an EFM encoder made by KENWOOD Co., Ltd. After the recording, signals were reproduced by the use of the same evaluation device. As a result, a reflectance was about 51%, an error rate was 7 cps, and a modulation amplitude was 0.65, and all of these values were good.

EXAMPLES 6 to 95

The same procedure as in Example 2 was conducted except that dipyrromethene metal chelate compounds (2-2 to 2-23, 3-2 to 3-13, 4-1 to 4-51, 5-1 to 5-37, 11-1 to 11-10, 12-1 to 12-10) mentioned in Table 1 were used, thereby forming optical record media..

Next, recording was carried out on the thus formed medium in the same manner as in Example 1 by the use of an optical disc evaluation device equipped with an evaluation device equipped with a semiconductor laser head of 635 nm made by Pulstech Industry Co., Ltd. and an EF4 encoder made by KENWOOD Co., Ltd. After the recording, signals were reproduced by the use of an evaluation device equipped with a red semiconductor laser head of 650 nm and 635 nm to measure a reflectance, an error rate and a modulation amplitude. As a result, all of the measured values were good.

Comparative Example 1

The same procedure as in Example 2 was conducted except that a dipyrromethene metal chelate compound (2-1) was replaced with pentamethinecyanine dye NK-2929 [1,3,3,1',3',3'hexamethyl-2',2'-(4,5,4'5'-dibenzo) indodicarbocyanine perchlorate, made by Japanese Photosensitive Dye Laboratory], thereby forming an optical recording medium. Next, recording was carried out on the thus formed medium at a linear velocity of 3.5 m/sec under a laser power of 7 mW in the same manner as in Example 1 by the use of an evaluation device (DDU-1000) equipped with a semiconductor laser head of 635 nm made by Pulstech Industry Co., Ltd. and an EFM encoder made by KENWOOD Co., Ltd. After the recording, signals were reproduced by the use of an evaluation device equipped with a red semiconductor laser head of 650 nm and 635 nm, and as a result, a reflectance was low, an error rate was large, and a modulation amplitude was small. In addition, when the reproduction was carried out for a long period of time, the signals deteriorated.

Comparative Example 2

The same procedure as in Comparative Example 1 was conducted except that NK-2929 was replaced with trimethinecyanine dye NK79 [1,3,3,1',3',3'-hexamethyl-2',2'-indodicarbocyanine iodide, made by Japanese Photosensitive Dye Laboratory], thereby forming an optical recording medium. Next, recording was carried out on the thus formed medium at a linear velocity of 3.5 m/sec under a laser power of 7 mW in the same manner as in Example 1 by the use of an evaluation device (DDU-1000) equipped with a semiconductor laser head of 635 nm made by Pulstech Industry Co., Ltd. and an EFM encoder made by KENWOOD Co., Ltd. After the recording, signals were reproduced by the use of an evaluation device equipped with a red semiconductor laser head of 650 nm and 635 nm, and as a result, a waveform was distorted, an error rate was large, and a modulation amplitude was small. In addition, when the reproduction was carried out for a long period of time, the signals deteriorated.

Table 2 shows the optical constants of the recording layers, the reflectances, the error rates and the modulation amplitudes in the case that the respective media were recorded at 635 nm and the reproduction was then carried out at 650 and 635 nm in Examples 1 to 4 and 6 to 95 as well as Comparative Examples 1 and 2.

TABLE 2-1

| | Example | | | | | | | |
|---|---|---|---|---|---|---|---|---|
| | 1 | 2 | 3 | 4 | 6 | 7 | 8 | 9 |
| Formula No. | 2-1 | 2-1 | 2-1 | 2-1 | 2-2 | 2-3 | 2-4 | 2-5 |
| Maximum absorption (nm) | 505 | 505 | 505 | 505 | 510 | 520 | 514 | 520 |
| Optical constant | | | | | | | | |
| At 650 nm | | | | | | | | |
| $n^{*1}$ | 2.2 | 2.2 | 2.2 | 2.2 | 2.0 | 2.1 | 2.1 | 2.0 |
| $\kappa^{*2}$ | 0.05 | 0.05 | 0.05 | 0.05 | 0.06 | 0.06 | 0.06 | 0.07 |
| At 635 nm | | | | | | | | |
| n | 2.3 | 2.3 | 2.3 | 2.3 | 2.3 | 2.3 | 2.5 | 2.4 |
| $\kappa$ | 0.07 | 0.07 | 0.07 | 0.07 | 0.08 | 0.09 | 0.10 | 0.11 |
| Reproduction properties of signals recorded at 635 nm | | | | | | | | |
| Reproduction at 650 nm | | | | | | | | |
| Reflectance (%) | 59 | 61 | 62 | 59 | 59 | 56 | 57 | 55 |
| Error rate (cps) | 8 | 7 | 5 | 8 | 9 | 10 | 10 | 12 |
| Modulation amplitude | 0.67 | 0.70 | 0.74 | 0.65 | 0.64 | 0.63 | 0.65 | 0.63 |
| Reproduction at 635 nm | | | | | | | | |
| Reflectance (%) | 59 | 58 | 61 | 57 | 58 | 56 | 55 | 54 |
| Error rate (cps) | 6 | 6 | 7 | 8 | 9 | 8 | 9 | 8 |
| Modulation amplitude | 0.76 | 0.78 | 0.76 | 0.66 | 0.66 | 0.64 | 0.66 | 0.65 |

$*^1$n; Refractive index
$*^2\kappa$; Extinction coefficient

TABLE 2-2

| | Example | | | | | | | |
|---|---|---|---|---|---|---|---|---|
| | 10 | 11 | 12 | 13 | 14 | 15 | 16 | 17 |
| Formula No. | 2-6 | 2-7 | 2-8 | 2-9 | 2-10 | 2-11 | 2-12 | 2-13 |
| Maximum absorption (nm) | 520 | 526 | 530 | 560 | 556 | 518 | 522 | 506 |
| Optical constant | | | | | | | | |
| At 650 nm | | | | | | | | |
| $n^{*1}$ | 2.2 | 2.1 | 2.0 | 2.1 | 2.2 | 2.0 | 2.0 | 2.1 |
| $\kappa^{*2}$ | 0.10 | 0.08 | 0.11 | 0.10 | 0.08 | 0.09 | 0.11 | 0.10 |
| At 635 nm | | | | | | | | |
| n | 2.5 | 2.4 | 2.5 | 2.4 | 2.5 | 2.4 | 2.4 | 2.4 |
| $\kappa$ | 0.12 | 0.12 | 0.13 | 0.13 | 0.10 | 0.12 | 0.12 | 0.11 |
| Reproduction properties of signals recorded at 635 nm | | | | | | | | |
| Reproduction at 650 nm | | | | | | | | |
| Reflectance (%) | 54 | 53 | 52 | 51 | 52 | 53 | 51 | 53 |
| Error rate (cps) | 9 | 9 | 10 | 9 | 9 | 10 | 9 | 9 |
| Modulation amplitude | 0.62 | 0.63 | 0.61 | 0.62 | 0.59 | 0.62 | 0.62 | 0.63 |
| Reproduction at 635 nm | | | | | | | | |
| Reflectance (%) | 57 | 59 | 60 | 55 | 56 | 57 | 58 | 55 |
| Error rate (cps) | 8 | 7 | 5 | 10 | 9 | 8 | 9 | 10 |
| Modulation amplitude | 0.66 | 0.67 | 0.68 | 0.67 | 0.66 | 0.65 | 0.64 | 0.63 |

$*^1$n; Refractive index
$*^2\kappa$; Extinction coefficient

TABLE 2-3

| | Example | | | | | | | |
|---|---|---|---|---|---|---|---|---|
| | 18 | 19 | 20 | 21 | 22 | 23 | 24 | 25 |
| Formula No. | 3-9 | 3-10 | 3-11 | 3-12 | 3-13 | 3-14 | 3-15 | 3-16 |
| Maximum absorption (nm) | 532 | 525 | 532 | 550 | 553 | 550 | 555 | 535 |
| Optical constant | | | | | | | | |
| At 650 nm | | | | | | | | |
| $n^{*1}$ | 2.1 | 2.2 | 2.1 | 2.2 | 2.1 | 2.1 | 2.2 | 2.0 |
| $\kappa^{*2}$ | 0.09 | 0.09 | 0.11 | 0.10 | 0.07 | 0.10 | 0.11 | 0.08 |
| At 635 nm | | | | | | | | |
| n | 2.6 | 2.5 | 2.4 | 2.4 | 2.5 | 2.6 | 2.4 | 2.5 |
| $\kappa$ | 0.11 | 0.11 | 0.11 | 0.12 | 0.10 | 0.12 | 0.13 | 0.10 |
| Reproduction properties of signals recorded at 635 nm | | | | | | | | |
| Reproduction at 650 nm | | | | | | | | |
| Reflectance (%) | 56 | 57 | 56 | 58 | 59 | 60 | 59 | 60 |
| Error rate (cps) | 9 | 10 | 11 | 9 | 9 | 11 | 10 | 11 |
| Modulation amplitude | 0.63 | 0.61 | 0.60 | 0.67 | 0.68 | 0.67 | 0.66 | 0.65 |
| Reproduction at 635 nm | | | | | | | | |
| Reflectance (%) | 54 | 55 | 56 | 57 | 58 | 57 | 56 | 57 |
| Error rate (cps) | 12 | 11 | 13 | 9 | 8 | 9 | 8 | 8 |
| Modulation amplitude | 0.63 | 0.62 | 0.64 | 0.72 | 0.70 | 0.71 | 0.69 | 0.69 |

$*^1$n; Refractive index
$*^2\kappa$; Extinction coefficient

TABLE 2-4

| | Example | | | | | | | |
|---|---|---|---|---|---|---|---|---|
| | 26 | 27 | 28 | 29 | 30 | 31 | 32 | 33 |
| Formula No. | 3-17 | 2-14 | 2-15 | 2-16 | 2-17 | 2-18 | 2-19 | 2-20 |
| Maximum absorption (nm) | 535 | 505 | 512 | 510 | 520 | 530 | 511 | 560 |
| Optical | | | | | | | | |

TABLE 2-4-continued

| | Example | | | | | | | |
|---|---|---|---|---|---|---|---|---|
| | 26 | 27 | 28 | 29 | 30 | 31 | 32 | 33 |
| constant | | | | | | | | |
| At 650 nm | | | | | | | | |
| $n^{*1}$ | 2.1 | 2.2 | 2.1 | 2.0 | 2.1 | 2.0 | 1.9 | 2.0 |
| $\kappa^{*2}$ | 0.10 | 0.10 | 0.09 | 0.10 | 0.10 | 0.08 | 0.09 | 0.08 |
| At 635 nm | | | | | | | | |
| n | 2.4 | 2.5 | 2.4 | 2.4 | 2.5 | 2.3 | 2.2 | 2.2 |
| κ | 0.10 | 0.11 | 0.10 | 0.12 | 0.11 | 0.09 | 0.08 | 0.08 |
| Reproduction properties of signals recorded at 635 nm | | | | | | | | |
| Reproduction at 650 nm | | | | | | | | |
| Reflectance (%) | 60 | 59 | 61 | 58 | 59 | 52 | 53 | 57 |
| Error rate (cps) | 9 | 8 | 7 | 9 | 8 | 10 | 11 | 9 |
| Modulation amplitude | 0.67 | 0.68 | 0.68 | 0.66 | 0.66 | 0.68 | 0.67 | 0.66 |
| Reproduction at 635 nm | | | | | | | | |
| Reflectance (%) | 58 | 59 | 60 | 57 | 59 | 59 | 58 | 57 |
| Error rate (cps) | 6 | 7 | 5 | 7 | 8 | 11 | 10 | 9 |
| Modulation amplitude | 0.70 | 0.71 | 0.69 | 0.68 | 0.68 | 0.64 | 0.62 | 0.63 |

$*^1$n; Refractive index
$*^2$κ; Extinction coefficient

TABLE 2-5

| | Example | | | | | | | |
|---|---|---|---|---|---|---|---|---|
| | 34 | 35 | 36 | 37 | 38 | 39 | 40 | 41 |
| Formula No. | 2-21 | 2-22 | 2-23 | 3-2 | 3-3 | 3-4 | 3-5 | 3-6 |
| Maximum absorption (nm) | 508 | 502 | 510 | 548 | 565 | 550 | 562 | 560 |
| Optical constant | | | | | | | | |
| At 650 nm | | | | | | | | |
| $n^{*1}$ | 1.9 | 1.8 | 1.9 | 1.9 | 1.8 | 2.0 | 2.1 | 1.9 |
| $\kappa^{*2}$ | 0.06 | 0.05 | 0.05 | 0.06 | 0.05 | 0.07 | 0.08 | 0.07 |
| At 635 nm | | | | | | | | |
| n | 2.1 | 2.2 | 2.0 | 2.1 | 2.2 | 2.1 | 2.1 | 2.2 |
| κ | 0.06 | 0.07 | 0.08 | 0.07 | 0.07 | 0.08 | 0.08 | 0.08 |
| Reproduction properties of signals recorded at 635 nm | | | | | | | | |
| Reproduction at 650 nm | | | | | | | | |
| Reflectance (%) | 52 | 53 | 50 | 49 | 54 | 52 | 51 | 50 |
| Error rate (cps) | 11 | 10 | 10 | 9 | 9 | 8 | 10 | 10 |
| Modulation amplitude | 0.57 | 0.56 | 0.55 | 0.56 | 0.57 | 0.58 | 0.59 | 0.59 |
| Reproduction at 635 nm | | | | | | | | |
| Reflectance (%) | 50 | 49 | 51 | 52 | 53 | 54 | 54 | 52 |
| Error rate (cps) | 10 | 10 | 9 | 9 | 10 | 9 | 11 | 10 |
| Modulation amplitude | 0.56 | 0.57 | 0.56 | 0.56 | 0.55 | 0.66 | 0.67 | 0.64 |

$*^1$n; Refractive index
$*^2$κ; Extinction coefficient

TABLE 2-6

| | Example | | | | | | | |
|---|---|---|---|---|---|---|---|---|
| | 42 | 43 | 44 | 45 | 46 | 47 | 48 | 49 |
| Formula No. | 3-7 | 3-8 | 12-1 | 11-1 | 11-2 | 11-3 | 11-4 | 11-5 |
| Maximum absorption (nm) | 530 | 528 | 580 | 576 | 585 | 592 | 580 | 580 |
| Optical constant | | | | | | | | |
| At 650 nm | | | | | | | | |
| $n^{*1}$ | 2.1 | 2.2 | 2.2 | 2.1 | 2.1 | 2.2 | 2.0 | 2.0 |
| $\kappa^{*2}$ | 0.05 | 0.06 | 0.04 | 0.06 | 0.07 | 0.05 | 0.06 | 0.06 |
| At 635 nm | | | | | | | | |
| n | 2.2 | 2.1 | 2.3 | 2.5 | 2.6 | 2.4 | 2.4 | 2.4 |
| κ | 0.07 | 0.08 | 0.06 | 0.10 | 0.12 | 0.13 | 0.10 | 0.10 |
| Reproduction properties of signals recorded at 635 nm | | | | | | | | |
| Reproduction at 650 nm | | | | | | | | |
| Reflectance (%) | 53 | 51 | 58 | 59 | 61 | 59 | 60 | 60 |
| Error rate (cps) | 9 | 10 | 9 | 9 | 9 | 10 | 11 | 11 |
| Modulation amplitude | 0.63 | 0.61 | 0.67 | 0.68 | 0.67 | 0.66 | 0.65 | 0.65 |
| Reproduction at 635 nm | | | | | | | | |
| Reflectance (%) | 54 | 53 | 57 | 58 | 57 | 56 | 57 | 57 |
| Error rate (cps) | 9 | 8 | 9 | 8 | 9 | 8 | 8 | 8 |
| Modulation amplitude | 0.66 | 0.64 | 0.72 | 0.70 | 0.71 | 0.69 | 0.69 | 0.69 |

$*^1$n; Refractive index
$*^2$κ; Extinction coefficient

TABLE 2-7

| | Example | | | | | | | |
|---|---|---|---|---|---|---|---|---|
| | 50 | 51 | 52 | 53 | 54 | 55 | 56 | 57 |
| Formula No. | 11-6 | 12-2 | 12-3 | 12-4 | 12-5 | 11-7 | 11-8 | 11-9 |
| Maximum absorption (nm) | 582 | 610 | 590 | 605 | 575 | 580 | 578 | 570 |
| Optical constant | | | | | | | | |
| At 650 nm | | | | | | | | |
| $n^{*1}$ | 2.1 | 2.2 | 2.1 | 2.0 | 2.1 | 2.0 | 1.9 | 2.0 |
| $\kappa^{*2}$ | 0.09 | 0.10 | 0.09 | 0.10 | 0.10 | 0.08 | 0.09 | 0.08 |
| At 635 nm | | | | | | | | |
| n | 2.5 | 2.5 | 2.4 | 2.4 | 2.5 | 2.3 | 2.3 | 2.3 |
| κ | 0.10 | 0.11 | 0.10 | 0.12 | 0.11 | 0.09 | 0.08 | 0.08 |

TABLE 2-7-continued

| | Example | | | | | | | |
|---|---|---|---|---|---|---|---|---|
| | 50 | 51 | 52 | 53 | 54 | 55 | 56 | 57 |
| Reproduction properties of signals recorded at 635 nm | | | | | | | | |
| Reproduction at 650 nm | | | | | | | | |
| Reflectance (%) | 60 | 59 | 61 | 58 | 59 | 58 | 59 | 58 |
| Error rate (cps) | 9 | 8 | 7 | 9 | 8 | 10 | 10 | 9 |
| Modulation amplitude | 0.67 | 0.68 | 0.68 | 0.66 | 0.66 | 0.68 | 0.67 | 0.66 |
| Reproduction at 635 nm | | | | | | | | |
| Reflectance (%) | 59 | 60 | 60 | 58 | 59 | 59 | 58 | 57 |
| Error rate (cps) | 6 | 7 | 5 | 7 | 8 | 11 | 10 | 9 |
| Modulation amplitude | 0.69 | 0.71 | 0.69 | 0.68 | 0.68 | 0.64 | 0.62 | 0.63 |

[1]n; Refractive index
[2]κ; Extinction coefficient

TABLE 2-8

| | Example | | | | | | | |
|---|---|---|---|---|---|---|---|---|
| | 58 | 59 | 60 | 61 | 62 | 63 | 64 | 65 |
| Formula No. | 11-10 | 12-6 | 12-7 | 12-8 | 12-9 | 12-10 | 4-1 | 4-2 |
| Maximum absorption (nm) | 580 | 600 | 604 | 596 | 600 | 610 | 552 | 555 |
| Optical constant | | | | | | | | |
| At 650 nm | | | | | | | | |
| n[1] | 2.0 | 1.9 | 2.0 | 1.9 | 2.0 | 2.0 | 2.1 | 2.2 |
| κ[2] | 0.06 | 0.05 | 0.05 | 0.06 | 0.05 | 0.07 | 0.04 | 0.04 |
| At 635 nm | | | | | | | | |
| n | 2.1 | 2.2 | 2.2 | 2.1 | 2.2 | 2.1 | 2.3 | 2.3 |
| κ | 0.06 | 0.07 | 0.08 | 0.07 | 0.07 | 0.08 | 0.06 | 0.06 |
| Reproduction properties of signals recorded at 635 nm | | | | | | | | |
| Reproduction at 650 nm | | | | | | | | |
| Reflectance (%) | 52 | 53 | 50 | 52 | 54 | 52 | 56 | 55 |
| Error rate (cps) | 11 | 10 | 10 | 9 | 9 | 8 | 9 | 10 |
| Modulation amplitude | 0.57 | 0.56 | 0.55 | 0.56 | 0.57 | 0.58 | 0.63 | 0.61 |
| Reproduction at 635 nm | | | | | | | | |
| Reflectance (%) | 50 | 49 | 51 | 52 | 53 | 54 | 54 | 54 |
| Error rate (cps) | 10 | 10 | 9 | 9 | 10 | 9 | 12 | 12 |
| Modulation amplitude | 0.56 | 0.57 | 0.56 | 0.56 | 0.55 | 0.66 | 0.63 | 0.64 |

[1]n; Refractive index
[2]κ; Extinction coefficient

TABLE 2-9

| | Example | | | | | | | |
|---|---|---|---|---|---|---|---|---|
| | 66 | 67 | 68 | 69 | 70 | 71 | 72 | 73 |
| Formula No. | 4-3 | 4-4 | 4-5 | 4-6 | 4-7 | 4-8 | 4-9 | 4-10 |
| Maximum absorption (nm) | 552 | 556 | 561 | 562 | 558 | 581 | 560 | 561 |
| Optical constant | | | | | | | | |
| At 650 nm | | | | | | | | |
| n[1] | 2.2 | 2.1 | 2.1 | 2.1 | 2.0 | 2.1 | 2.2 | 2.1 |
| κ[2] | 0.04 | 0.05 | 0.07 | 0.04 | 0.06 | 0.04 | 0.05 | 0.04 |
| At 635 nm | | | | | | | | |
| n | 2.2 | 2.6 | 2.5 | 2.3 | 2.5 | 2.1 | 2.3 | 2.5 |
| κ | 0.06 | 0.11 | 0.12 | 0.12 | 0.10 | 0.05 | 0.06 | 0.06 |
| Reproduction properties of signals recorded at 635 nm | | | | | | | | |
| Reproduction at 650 nm | | | | | | | | |
| Reflectance (%) | 60 | 58 | 60 | 61 | 59 | 55 | 57 | 55 |
| Error rate (cps) | 9 | 9 | 8 | 10 | 10 | 9 | 10 | 10 |
| Modulation amplitude | 0.65 | 0.68 | 0.66 | 0.67 | 0.65 | 0.62 | 0.61 | 0.61 |
| Reproduction at 635 nm | | | | | | | | |
| Reflectance (%) | 56 | 58 | 58 | 56 | 56 | 56 | 55 | 55 |
| Error rate (cps) | 10 | 10 | 9 | 8 | 9 | 12 | 11 | 13 |
| Modulation amplitude | 0.71 | 0.70 | 0.70 | 0.69 | 0.68 | 0.61 | 0.62 | 0.64 |

[1]n; Refractive index
[2]κ; Extinction coefficient

TABLE 2-10

| | Example | | | | | | | |
|---|---|---|---|---|---|---|---|---|
| | 74 | 75 | 76 | 77 | 78 | 79 | 80 | 81 |
| Formula No. | 4-11 | 4-12 | 4-13 | 4-14 | 4-15 | 4-47 | 4-48 | 4-51 |
| Maximum absorption (nm) | 567 | 570 | 570 | 568 | 566 | 565 | 568 | 580 |
| Optical constant | | | | | | | | |
| At 650 nm | | | | | | | | |
| n[1] | 2.2 | 2.0 | 2.3 | 2.2 | 2.0 | 2.3 | 2.2 | 2.3 |
| κ[2] | 0.03 | 0.06 | 0.06 | 0.05 | 0.05 | 0.06 | 0.05 | 0.05 |
| At 635 nm | | | | | | | | |
| n | 2.3 | 2.7 | 2.6 | 2.4 | 2.6 | 2.6 | 2.4 | 2.6 |
| κ | 0.05 | 0.10 | 0.12 | 0.12 | 0.11 | 0.12 | 0.12 | 0.11 |
| Reproduction properties of signals recorded at 635 nm | | | | | | | | |
| Reproduction at 650 nm | | | | | | | | |
| Reflectance (%) | 58 | 59 | 60 | 59 | 61 | 60 | 59 | 61 |
| Error rate (cps) | 9 | 8 | 9 | 10 | 10 | 9 | 10 | 10 |

TABLE 2-10-continued

| | Example | | | | | | | |
|---|---|---|---|---|---|---|---|---|
| | 74 | 75 | 76 | 77 | 78 | 79 | 80 | 81 |
| Modulation amplitude | 0.65 | 0.69 | 0.67 | 0.65 | 0.64 | 0.67 | 0.65 | 0.64 |
| Reproduction at 635 nm | | | | | | | | |
| Reflectance (%) | 57 | 60 | 57 | 56 | 58 | 57 | 56 | 58 |
| Error rate (cps) | 9 | 8 | 9 | 8 | 8 | 9 | 8 | 8 |
| Modulation amplitude | 0.71 | 0.69 | 0.71 | 0.67 | 0.69 | 0.71 | 0.67 | 0.69 |

[1]n; Refractive index
[2]κ; Extinction coefficient

TABLE 2-11

| | Example | | | | | | | |
|---|---|---|---|---|---|---|---|---|
| | 82 | 83 | 84 | 85 | 86 | 87 | 88 | 89 |
| Formula No. | 5-1 | 5-2 | 5-3 | 5-4 | 5-5 | 5-6 | 5-7 | 5-8 |
| Maximum absorption (nm) | 576 | 584 | 578 | 580 | 589 | 575 | 573 | 573 |
| Optical constant | | | | | | | | |
| At 650 nm | | | | | | | | |
| n[1] | 2.2 | 2.2 | 2.2 | 2.3 | 2.1 | 2.2 | 2.2 | 2.0 |
| κ[2] | 0.05 | 0.04 | 0.06 | 0.04 | 0.05 | 0.07 | 0.07 | 0.06 |
| At 635 nm | | | | | | | | |
| n | 2.4 | 2.3 | 2.3 | 2.4 | 2.5 | 2.6 | 2.3 | 2.4 |
| κ | 0.07 | 0.06 | 0.05 | 0.06 | 0.10 | 0.11 | 0.11 | 0.10 |
| Reproduction properties of signals recorded at 635 nm | | | | | | | | |
| Reproduction at 650 nm | | | | | | | | |
| Reflectance (%) | 57 | 57 | 56 | 60 | 59 | 61 | 61 | 60 |
| Error rate (cps) | 9 | 11 | 11 | 10 | 9 | 8 | 8 | 11 |
| Modulation amplitude | 0.62 | 0.62 | 0.60 | 0.69 | 0.68 | 0.67 | 0.65 | 0.65 |
| Reproduction at 635 nm | | | | | | | | |
| Reflectance (%) | 53 | 55 | 58 | 55 | 58 | 60 | 56 | 58 |
| Error rate (cps) | 9 | 11 | 13 | 9 | 10 | 9 | 8 | 6 |
| Modulation amplitude | 0.62 | 0.62 | 0.64 | 0.71 | 0.69 | 0.71 | 0.70 | 0.69 |

[1]n; Refractive index
[2]κ; Extinction coefficient

TABLE 2-12

| | Example | | | | | | Comp. Ex. 1 | Comp. Ex. 2 |
|---|---|---|---|---|---|---|---|---|
| | 90 | 91 | 92 | 93 | 94 | 95 | | |
| Formula No. | 5-9 | 5-10 | 5-11 | 5-12 | 5-13 | 5-14 | NK2929 | NK79 |
| Maximum absorption (nm) | 575 | 573 | 579 | 577 | 579 | 576 | 640 | 550 |
| Optical constant | | | | | | | | |
| At 650 nm | | | | | | | | |
| n[1] | 2.3 | 2.2 | 2.0 | 2.2 | 2.1 | 2.2 | 1.9 | 2.1 |
| κ[2] | 0.05 | 0.04 | 0.06 | 0.04 | 0.05 | 0.07 | 1.35 | 0.08 |
| At 635 nm | | | | | | | | |
| n | 2.4 | 2.3 | 2.2 | 2.3 | 2.4 | 2.6 | 1.8 | 2.3 |
| κ | 0.05 | 0.06 | 0.06 | 0.05 | 0.11 | 0.06 | 1.30 | 0.10 |
| Reproduction properties of signals recorded at 635 nm | | | | | | | | |
| Reproduction at 650 nm | | | | | | | | |
| Reflectance (%) | 55 | 57 | 59 | 58 | 59 | 60 | 9 | 56 |
| Error rate (cps) | 8 | 9 | 11 | 10 | 9 | 8 | 3000 | 550 |
| Modulation amplitude | 0.63 | 0.64 | 0.60 | 0.66 | 0.68 | 0.65 | 0.13 | 0.35 |
| Reproduction at 635 nm | | | | | | | | |
| Reflectance (%) | 52 | 55 | 54 | 57 | 60 | 57 | 9 | 60 |
| Error rate (cps) | 12 | 10 | 13 | 11 | 8 | 10 | 2500 | 350 |
| Modulation amplitude | 0.62 | 0.62 | 0.65 | 0.67 | 0.70 | 0.69 | 0.15 | 0.38 |

[1]n; Refractive index
[2]κ; Extinction coefficient

EXAMPLE 96

4.8 g of 1-formyl-3-phenylisoindole and 2.3 g of 2,4-dimethylpyrrole were dissolved in 500 ml of ethanol under nitrogen stream, and 4.1 g of 47% hydrobromic acid was added dropwise thereto, followed by stirring at a reflux temperature for 2 hours. After the solution was cooled to room temperature, the precipitated crystals were collected by filtration, and then washed with ethanol and water to obtain 6.5 g of a compound represented by the following formula (1-a):

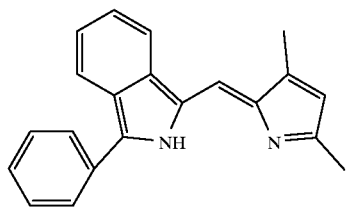
(1-a)

Next, 2.8 g of a compound represented by formula (1-a) was dissolved in 600 ml of ethanol, and 1.8 g of cobalt acetate tetrahydrate was added thereto, followed by stirring at a reflux temperature for 2 hours. After cooling, the precipitated is crystals were collected by filtration, washed with water, and then recrystallized from ethanol to obtain 0.8 g of a compound represented by formula (4-1):

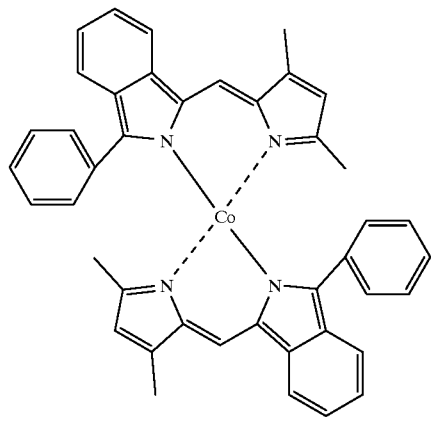
(4-1)

From the following analytical results, it was confirmed that the obtained product was a desired compound.

Results of elemental analysis ($C_{42}H_{34}N_4Co$)

|  | C | H | N |
|---|---|---|---|
| Calcd. (%) | 77.17 | 5.24 | 8.57 |
| Found (%) | 78.50 | 5.76 | 8.69 |

MS (m/e): 654 (M$^+$)

The thus obtained compound showed a maximum absorption at 545 nm in a chloroform solution, and had a gram extinction coefficient of $1.46 \times 10^5$ ml/g·cm.

EXAMPLE 97

5.5 g of 1-formyl-3-(4-methoxphenyl)isoindole and 2.3 g of 2,4-dimethylpyrrole were dissolved in 500 ml of ethanol under nitrogen stream, and 4.2 g of 47% hydrobromic acid was added dropwise thereto, followed by stirring at a reflux temperature for 2 hours. After the solution was cooled to room temperature, the precipitated crystals were collected by filtration, and then washed with ethanol and water to obtain 6.4 g of a compound represented by the following formula (1-b):

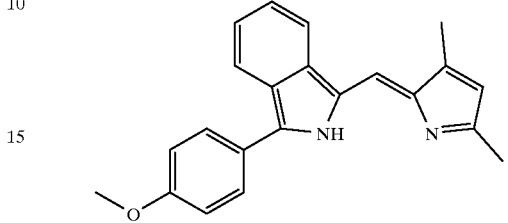
(1-b)

Next, 3.0 g of a compound represented by formula (1-b) was dissolved in 700 ml of ethanol, and 2.0 g of cobalt acetate tetrahydrate was added thereto, followed by stirring at a reflux temperature for 2 hours. After cooling, the precipitated crystals were collected by filtration, washed with water, and then recrystallized from ethanol to obtain 1.1 g of a compound represented by formula (4-2):

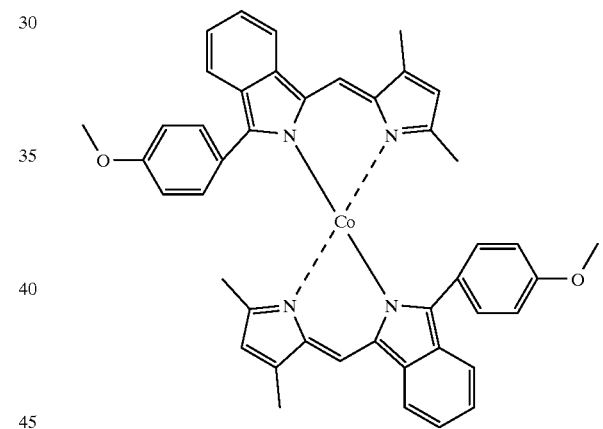
(4-2)

From the following analytical results, it was confirmed that the obtained product was a desired compound.

Results of elemental analysis ($C_{44}H_{38}N_4Co$)

|  | C | H | N |
|---|---|---|---|
| Calcd. (%) | 77.52 | 5.62 | 8.22 |
| Found (%) | 76.91 | 5.60 | 8.19 |

MS (m/e): 682 (M$^+$)

The thus obtained compound showed a maximum absorption at 547 nm in a chloroform solution, and had a gram extinction coefficient of $1.20 \times 10^5$ ml/g·cm.

EXAMPLE 98

2.8 g of a compound represented by formula (1-a) was dissolved in 500 ml of ethanol, and 1.5 g of zinc acetate was added thereto, followed by stirring at a reflux temperature for 2 hours. After cooling, the precipitated crystals were collected by filtration, washed with water, and then recrystallized from ethanol to obtain 1.6 g of a compound represented by the following formula (4-3):

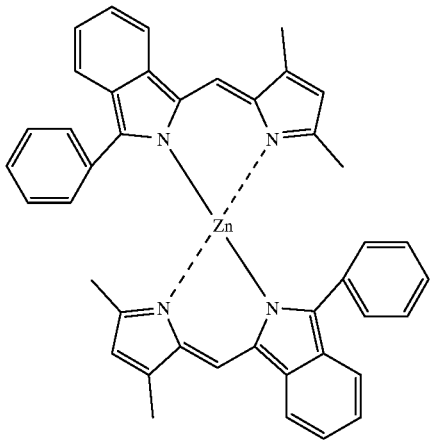

(4-3)

From the following analytical results, it was confirmed that the obtained product was a desired compound.

Results of elemental analysis ($C_{42}H_{34}N_4Zn$)

|  | C | H | N |
|---|---|---|---|
| Calcd. (%) | 76.42 | 5.19 | 8.49 |
| Found (%) | 76.58 | 5.59 | 8.71 |

MS (m/e): 660 (M+)

The thus obtained compound showed a maximum absorption at 545 nm in a chloroform solution, and had a gram extinction coefficient of $2.01 \times 10^5$ ml/g·cm.

EXAMPLE 99

5.0 g of 1-formyl-3-(4-tert-butylphenylthio)isoindole and 1.7 g of 2,4-dimethylpyrrole were dissolved in 500 ml of ethanol under nitrogen stream, and 3.1 g of 47% hydrobromic acid was added dropwise thereto, followed by stirring at a reflux temperature for 2 hours. After the solution was cooled to room temperature, the precipitated crystals were collected by filtration, and then washed with ethanol and water to obtain 3.9 g of a compound represented by the following formula (1-c):

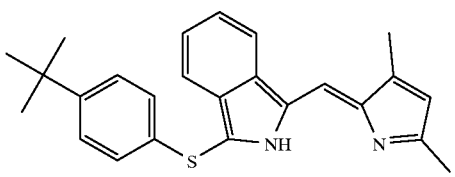

(1-c)

Next, 0.5 g of a compound represented by formula (1-c) was dissolved in 150 ml of ethanol, and 0.3 g of cobalt acetate tetrahydrate was added thereto, followed by stirring at a reflux temperature for 2 hours. After cooling, the precipitated crystals were collected by filtration, washed with water, and then recrystallized from ethanol to obtain 0.4 g of a compound represented by formula (4-4):

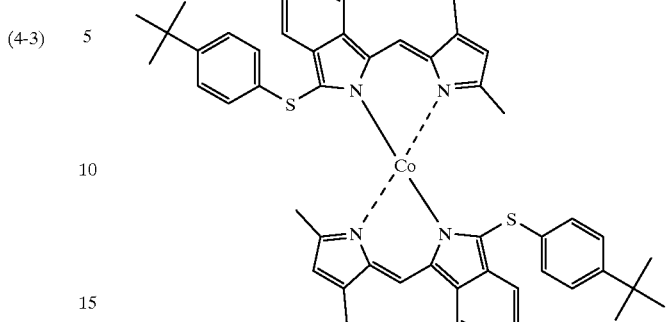

(4-4)

From the following analytical results, it was confirmed is that the obtained product was a desired compound.

Results of elemental analysis ($C_{50}H_{50}N_4S_2Co$)

|  | C | H | N |
|---|---|---|---|
| Calcd. (%) | 72.35 | 6.07 | 6.75 |
| Found (%) | 71.16 | 6.06 | 6.59 |

MS (m/e): 830 (M+)

The thus obtained compound showed a maximum absorption at 550 nm in a chloroform solution, and had a gram extinction coefficient of $1.24 \times 10^5$ ml/g·cm.

EXAMPLE 100

4.8 g of 1-formyl-3-phenylisoindole and 2.9 g of 2,4-dimethyl-3-ethylpyrrole were dissolved in 600 ml of ethanol under nitrogen stream, and 4.1 g of 47% hydrobromic acid was added dropwise thereto, followed by stirring at a reflux temperature for 2 hours. After the solution was cooled to room temperature, the precipitated crystals were collected by filtration, and then washed with ethanol and water to obtain 6.8 g of a compound represented by the following formula (1-d):

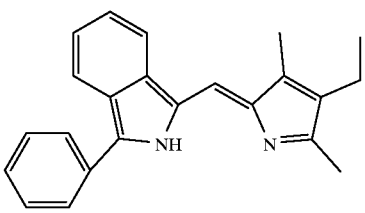

(1-d)

Next, 2.8 g of a compound represented by formula (1-d) was dissolved in 700 ml of ethanol, and 1.9 g of cobalt acetate tetrahydrate was added thereto, followed by stirring at a reflux temperature for 2 hours. After cooling, the precipitated crystals were collected by filtration, washed with water, and then recrystallized from ethanol to obtain 1.7 g of a compound represented by formula (4-5):

(4-5)

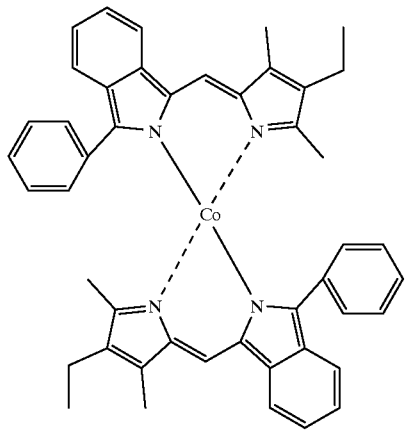

From the following analytical results, it was confirmed that the obtained product was a desired compound.

Results of elemental analysis ($C_{46}H_{42}N_4Co$)

|  | C | H | N |
|---|---|---|---|
| Calcd. (%) | 77.84 | 5.96 | 7.89 |
| Found (%) | 77.60 | 6.03 | 7.91 |

MS (m/e): 710 (M$^+$)

The thus obtained compound showed a maximum absorption at 555 nm in a chloroform solution, and had a gram extinction coefficient of $1.47 \times 10^5$ ml/g·cm.

EXAMPLE 101

2.8 g of a compound represented by formula (1-d) was dissolved in 700 ml of ethanol, and 1.4 g of zinc acetate was added thereto, followed by stirring at a reflux temperature for 2 hours. After cooling, the precipitated crystals were collected by filtration, washed with water, and then recrystallized from ethanol to obtain 2.1 g of a compound represented by the following formula (4-6):

(4-6)

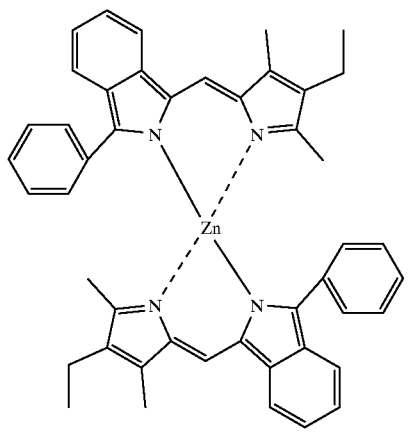

From the following analytical results, it was confirmed that the obtained product was a desired compound.

Results of elemental analysis ($C_{46}H_{42}N_4Zn$)

|  | C | H | N |
|---|---|---|---|
| Calcd. (%) | 77.14 | 5.91 | 7.82 |
| Found (%) | 76.96 | 6.01 | 8.31 |

MS (m/e): 716 (M$^+$)

The thus obtained compound showed a maximum absorption at 554 nm in a chloroform solution, and had a gram extinction coefficient of $1.83 \times 10^5$ ml/g·cm.

EXAMPLE 102

0.9 g of a compound represented by formula (1-c) was dissolved in 200 ml of ethanol, and 0.4 g of zinc acetate was added thereto, followed by stirring at a reflux temperature for 2 hours. After cooling, the precipitated crystals were collected by filtration, washed with water, and then recrystallized from ethanol to obtain 0.7 g of a compound represented by the following formula (4-7):

(4-7)

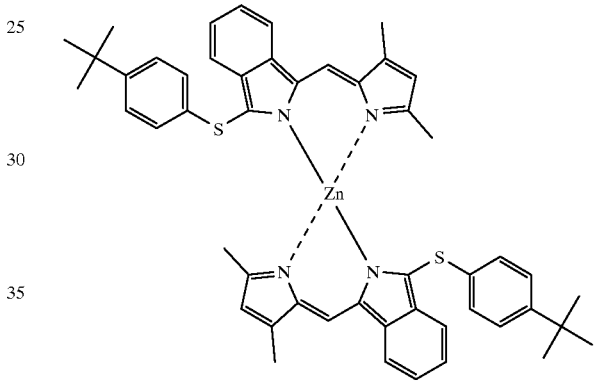

From the following analytical results, it was confirmed that the obtained product was a desired compound.

Results of elemental analysis ($C_{50}H_{50}N_4S_2Zn$)

|  | C | H | N |
|---|---|---|---|
| Calcd. (%) | 71.79 | 6.02 | 6.70 |
| Found (%) | 71.25 | 5.92 | 6.43 |

MS (m/e): 837 (M$^+$)

The thus obtained compound showed a maximum absorption at 550 nm in a chloroform solution, and had a gram extinction coefficient of $2.33 \times 10^5$ ml/g·cm.

EXAMPLE 103

2.0 g of a compound represented by formula (1-c) and 0.4 g of potassium cyanide were dissolved in 300 ml of ethanol, followed by stirring at a reflux temperature for 7 hours. After the solution was cooled to room temperature, 300 ml of water and 5 g of rhodefine were added, and the precipitated crystals were collected by filtration, and then washed with water. The thus filtered agglomerates were dissolved in 100 ml of chloroform, and a chloroform solution containing 0.7 g of bromine was added dropwise at room temperature. After stirring at room temperature for 10 minutes, the solution was concentrated, and then purified through column chromatography (silica gel-methanol:chloroform=1:20) to obtain 1.4 g of a compound represented by the following formula (1-e):

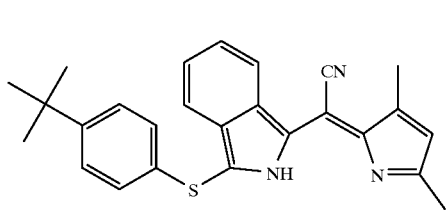

(1-e)

Next, 1.0 g of a compound represented by formula (1-e) was dissolved in 300 ml of ethanol, and 0.4 g of copper acetate was added thereto, followed by stirring at a reflux temperature for 2 hours. After cooling, the precipitated crystals were collected by filtration, washed with water, and then recrystallized from ethanol to obtain 0.5 g of a compound represented by formula (4-8):

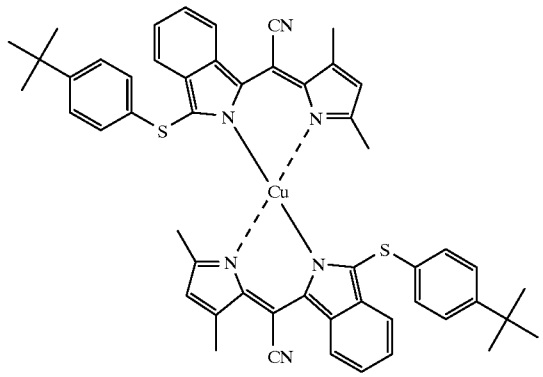

(4-8)

From the following analytical results, it was confirmed that the obtained product was a desired compound.

Results of elemental analysis ($C_{52}H_{48}N_6S_2Cu$)

|  | C | H | N |
|---|---|---|---|
| Calcd.(%) | 70.60 | 5.47 | 9.50 |
| Found (%) | 71.21 | 5.39 | 9.46 |

MS (m/e): 885 (M$^+$)

The thus obtained compound showed a maximum absorption at 574 nm in a chloroform solution, and had a gram extinction coefficient of $1.12 \times 10^5$ ml/g·cm.

EXAMPLE 104

2.0 g of a compound represented by formula (1-a) was dissolved in 50 ml of dichloromethane, and 1.4 g of N,N-diisopropylethylamine was added thereto, followed by stirring at room temperature for 30 minutes. Afterward, 1.6 g of boron trifluoride ethyl ether complex was added, followed by stirring for 2 hours. After water washing, dichloromethane was distilled off, and the solution was then purified through column chromatography (silica gel-methanol:chloroform=1:20) to obtain 0.9 g of a compound represented by the following formula (5-1):

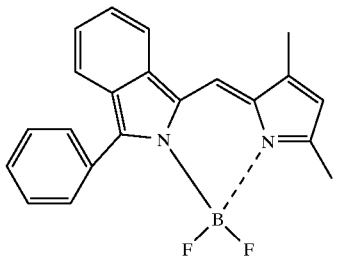

(5-1)

From the following analytical results, it was confirmed that the obtained product was a desired compound.

Results of elemental analysis ($C_{21}H_{17}N_2BF_2$)

|  | C | H | N |
|---|---|---|---|
| Calcd.(%) | 72.86 | 4.95 | 8.09 |
| Found (%) | 72.23 | 5.17 | 7.99 |

MS (m/e): 346 (M$^+$)

The thus obtained compound showed a maximum absorption at 569 nm in a chloroform solution, and had a gram extinction coefficient of $2.26 \times 10^5$ ml/g·cm.

EXAMPLE 105

2.0 g of a compound represented by formula (1-b) was dissolved in 50 ml of dichloromethane, and 1.4 g of N,N-diisopropylethylamine was added thereto, followed by stirring at room temperature for 30 minutes. Afterward, 1.5 g of boron trifluoride ethyl ether complex was added, followed by stirring for 2 hours. After water washing, dichloromethane was distilled off, and the solution was then purified through column chromatography (silica gel-methanol:chloroform=1:20) to obtain 0.8 g of a compound represented by the following formula

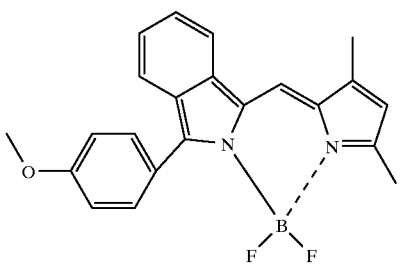

(5-2)

From the following analytical results, it was confirmed that the obtained product was a desired compound.

Results of elemental analysis ($C_{22}H_{19}N_2OBF_2$)

|  | C | H | N |
|---|---|---|---|
| Calcd. (%) | 70.24 | 5.09 | 7.45 |
| Found (%) | 70.54 | 5.32 | 7.41 |

MS (m/e): 346 (M$^+$)

The thus obtained compound showed a maximum absorption at 576 nm in a chloroform solution, and had a gram extinction coefficient of $2.13 \times 10^5$ ml/g·cm.

What is claimed is:

1. An optical recording medium having at least a recording layer and a reflective layer on a substrate, said recording layer containing a dipyrromethene metal chelate compound represented by formula (2):

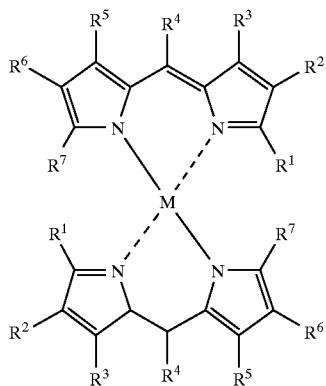

(2)

wherein $R^1$ to $R^7$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkyoxy group having 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonyl group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 to 20 carbon atoms, alkylthio group having 1 to 20 carbon atoms, phenylthio group having 6 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(hydroxyalkyl)aminocarbonyl group having 2 to 20 carbon atoms, di(hydroxyalkyl)aminocarbonyl group having 3 to 20 carbon atoms, mono(alkoxyalkyl)aminocarbonyl group having 3 to 20 carbon atoms or di(alkyoxyalkyl)aminocarbonyl group having 5 to 20 carbon atoms; $R^2$ and $R^3$ and/or $R^5$ and $R^6$ may bond to each other to form an aromatic ring fused to a pyrrole ring; and the fused aromatic rings formed by these groups may be the same or different and are represented by formula (a):

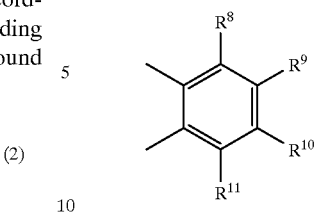

(a)

wherein $R^8$ to $R^{11}$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkoxy group having 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonylamino group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 to 20 carbon atoms, alkylthio group having 1 to 20 carbon atoms, phenylthio group having 1 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(hydroxyalkyl)aminocarbonyl group having 2 to 20 carbon atoms, di(hydroxyalkyl) aminocarbonyl group having 3 to 20 carbon atoms, mono (alkoxyalkyl)aminocarbonyl group having 3 to 20 carbon atoms or di(alkoxyalkyl)aminoocarbonyl group having 5 to 20 carbon atoms; $R^{10}$ and $R^{11}$ may bond to each other to form an aromatic ring; and M is a transition metal.

2. The optical recording medium according to claim 1 which is recordable and reproducible by a laser light selected from the wavelength range of 520 to 690 nm.

3. The optical recording medium according to claim 1 wherein, at a laser wavelength, a refractive index of the recording layer is 1.8 or more, and an extinction coefficient of the recording layer is in the range of 0.04 to 0.40.

4. The optical recording medium according to claim 1 wherein a reflectance of a laser light selected from the wavelength range of 520 to 690 nm is 20% or more as measured from the side of the substrate.

5. An optical recording medium having at least a recording layer and a reflective layer on a substrate, said recording layer containing a dipyrromethene metal chelate compound represented by formula (3):

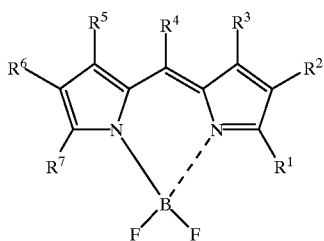

(3)

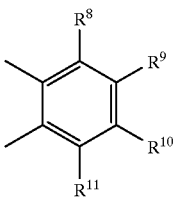

(a)

wherein $R^1$ to $R^7$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkoxy group having 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonyl group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 o 20 carbon atoms, alkylthio group having 1 to 20 carbon atoms, phenylthio group having 6 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(bydroxyalkyl)aminocarbonyl group having 2 to 20 carbon atoms, di(hydroxyalkyl)aminocarbonyl group having 3 to 20 carbon atoms, mono(alkoxyalkyl)aminocarbonyl group having 3 to 20 carbon atoms or di(alkoxyalkyl)aminocarbonyl group having 5 to 20 carbon atoms; $R^2$ and $R^3$ and/or $R^5$ and $R^6$ may bond to each other to form an aromatic ring fused to a pyrrole ring; and the fused aromatic rings formed by these groups may be the same or different and are represented by formula (a):

wherein $R^8$ and $R^{11}$ are each independently a hydrogen atom, halogen atom, nitro group, cyano group, hydroxyl group, amino group, carboxyl group, sulfonic acid group, alkyl group having 1 to 20 carbon atoms, halogenoalkyl group having 1 to 20 carbon atoms, alkoxy group having 1 to 20 carbon atoms, alkenyl group having 2 to 20 carbon atoms, alkoxyalkyl group having 2 to 20 carbon atoms, alkoxyalkoxy group 2 to 20 carbon atoms, aryloxy group having 6 to 20 carbon atoms, acyl group having 1 to 20 carbon atoms, alkoxycarbonyl group having 2 to 20 carbon atoms, alkylaminocarbonyl group having 2 to 20 carbon atoms, dialkylaminocarbonyl group having 3 to 20 carbon atoms, alkylcarbonylamino group having 2 to 20 carbon atoms, phenylcarbonylamino group having 7 to 20 carbon atoms, phenylaminocarbonyl group having 7 to 20 carbon atoms, phenoxycarbonyl group having 7 to 20 carbon atoms, aralkyl group having 7 to 20 carbon atoms, aryl group having 6 to 20 carbon atoms, heteroaryl group having 5 to 20 carbon atoms, alkylthio group having 1 to 20 carbon atoms, phenylthio group having 6 to 20 carbon atoms, alkenyloxycarbonyl group having 3 to 20 carbon atoms, aralkyloxycarbonyl group having 8 to 20 carbon atoms, alkoxycarbonylalkoxycarbonyl group having 4 to 20 carbon atoms, alkylcarbonylalkoxycarbonyl group having 4 to 20 carbon atoms, mono(hydroxyalkyl)aminocarbonyl group having 2 to 20 carbon atoms, di(hydroxyalkyl) aminocarbonyl group having 3 to 20 carbon atoms, mono (alkoxyalkyl)aminocarbonyl group having 3 to 20 carbon atoms or di(alkoxyalkyl)aminocarbonyl group having 5 to 20 carbon atoms; and $R^{10}$ and $R^{11}$ may bond to each other to form an aromatic ring.

6. The optical recording medium according to claim 5 which is recordable and reproducible by a laser light selected from the wavelength range of 520 to 690 nm.

7. The optical recording medium according to claim 5 wherein, at a laser wavelength, a refractive index of the recording layer is 1.8 or more, and an extinction coefficient of the recording layer is in the range of 0.04 to 0.40.

8. The optical recording medium according to claim 5 wherein a reflectance of a laser light selected from the wavelength range of 520 to 690 nm is 20% or more as measured from the side of the substrate.

* * * * *

UNITED STATES PATENT AND TRADEMARK OFFICE
CERTIFICATE OF CORRECTION

PATENT NO. : 5,948,593
DATED : September 7, 1999
INVENTOR(S) : Tsutami MISAWA et al.

It is certified that error appears in the above-identified patent and that said Letters Patent is hereby corrected as shown below:

Column 73, line 41, replace "mono(bydroxyalkyl)aminocarbonyl" with --mono(hydroxyalkyl)aminocarbonyl--.

Column 74, line 12, replace "$R^8$ and $R^{11}$" with --$R^8$ to $R^{11}$--.

Signed and Sealed this

Twenty-ninth Day of May, 2001

Attest:

NICHOLAS P. GODICI

*Attesting Officer*  *Acting Director of the United States Patent and Trademark Office*